US012708284B2

(12) United States Patent
Skak et al.

(10) Patent No.: US 12,708,284 B2
(45) Date of Patent: Aug. 18, 2026

(54) DRUG DELIVERY DEVICE WITH CARRIER AND INSERT

(71) Applicant: Biograil APS, Roskilde (DK)

(72) Inventors: Nikolaj Skak, Roskilde (DK); Karsten Lindhardt, Roskilde (DK); Kamille Majken Dumong Erichsen, Roskilde (DK)

(73) Assignee: Biograil APS, Roskilde (DK)

( * ) Notice: Subject to any disclaimer, the term of this patent is extended or adjusted under 35 U.S.C. 154(b) by 379 days.

(21) Appl. No.: 18/260,862

(22) PCT Filed: Jan. 28, 2022

(86) PCT No.: PCT/EP2022/052050
§ 371 (c)(1),
(2) Date: Jul. 10, 2023

(87) PCT Pub. No.: WO2022/162146
PCT Pub. Date: Aug. 4, 2022

(65) Prior Publication Data
US 2024/0074672 A1 Mar. 7, 2024

(30) Foreign Application Priority Data
Jan. 29, 2021 (DK) ............................ PA202170041

(51) Int. Cl.
*A61B 5/00* (2006.01)
*A61B 5/07* (2006.01)
(Continued)

(52) U.S. Cl.
CPC ............ *A61B 5/073* (2013.01); *A61B 5/6861* (2013.01); *A61M 31/002* (2013.01);
(Continued)

(58) Field of Classification Search
CPC ..... A61B 5/073; A61B 5/6861; A61B 5/6882; A61M 31/002; A61M 37/00; A61M 2205/103
See application file for complete search history.

(56) References Cited

U.S. PATENT DOCUMENTS

2009/0012530 A1 1/2009 Fowler
2010/0286668 A1* 11/2010 Tanaka ................ A61M 31/002 604/891.1
(Continued)

FOREIGN PATENT DOCUMENTS

WO WO 2009/063377 A1 5/2009
WO WO 2012/125901 A1 9/2012
(Continued)

OTHER PUBLICATIONS

International Search Report for PCT/EP2022/052050 dated May 27, 2022.

*Primary Examiner* — David N Brandt
(74) *Attorney, Agent, or Firm* — KNOBBE, MARTENS, OLSON & BEAR, LLP

(57) ABSTRACT

A drug delivery device having an axis, the drug delivery device comprising a carrier and an insert, the carrier comprising a first body part having a first recess, a first attachment part attached to the first body part and having a first distal end, a second body part having a second recess an actuator mechanism configured to rotate at least one of the first body part or the second body part with respect to one another about the axis, and an insert configured to be inserted and fixed in the second recess, the insert comprising a second attachment part and an insert body with an insert recess, the second attachment part having a second distal end.

16 Claims, 10 Drawing Sheets

(51) Int. Cl.
*A61M 31/00* (2006.01)
*A61M 37/00* (2006.01)

(52) U.S. Cl.
CPC ............ *A61B 5/6882* (2013.01); *A61M 37/00* (2013.01); *A61M 2205/103* (2013.01)

(56) References Cited

U.S. PATENT DOCUMENTS

2011/0166416 A1 7/2011 Katayma et al.
2011/0207998 A1* 8/2011 Katayama .............. A61B 1/041 600/106
2016/0136104 A1* 5/2016 Niichel .............. A61K 41/0028 424/452
2017/0258732 A1 9/2017 Imran et al.
2020/0222318 A1 7/2020 Imran et al.
2022/0118056 A1* 4/2022 Imran .................. A61K 9/0053

FOREIGN PATENT DOCUMENTS

WO WO 2018/112232 A1 6/2018
WO WO 2019/121686 A1 6/2019
WO WO 2021/013907 A1 1/2021

* cited by examiner

DRUG DELIVERY DEVICE WITH CARRIER AND INSERT

CROSS REFERENCE TO RELATED APPLICATIONS

This application is a U.S. National Phase Application of PCT International Application Number PCT/EP2022/052050, filed on Jan. 28, 2022, designating the United States of America and published in the English language, which is an International Application of and claims the benefit of priority to Danish Patent Application No. PA202170041, filed on Jan. 29, 2021. The disclosures of the above-referenced applications are hereby expressly incorporated by reference in their entireties.

The present disclosure relates to a drug delivery device and in particular to a drug delivery device for oral administration. The drug delivery device is advantageously configured for delivery of an active drug substance in the gastrointestinal tract including the stomach and/or intestines, such as the small intestines, duodenum, jejunum, caecum, and/or the large intestines (colon).

BACKGROUND

A number of for example low permeable and/or low water soluble active drug substances are currently delivered by i.e. subcutaneous, intradermal, intramuscular, rectal, vaginal or intravenous route. Oral administration has the potential for the widest patient acceptance and compliance and thus attempts to deliver low permeable and/or low water soluble active drug substances through the preferred oral route of administration has been tried but with limited success in particular due to lack of stability and limited absorption from the gastrointestinal tract.

Stability both relates to the stability of the active drug substance during manufacturing and storage of the delivery device, and to the stability of the active drug substance during the passage in the gastrointestinal tract before it become available for absorption.

Limited gastrointestinal absorption is due to the gastrointestinal wall barrier preventing active drug substance from being absorbed after oral dosing because of the low permeability of the active drug substance, which is for example due to pre-systemic metabolism, size and/or the charges and/or because of the water solubility of the active drug substance.

Multiple approaches to solve these stability and absorption challenges have been suggested, but an effective solution to the challenges remain unresolved.

SUMMARY

Thus, there is an unmet need to provide a drug delivery device, which is capable of delivering drug substances for absorption in the gastrointestinal tissue. More generally, there remains a need for drug products and methods that enable enhanced drug delivery, when drug products are administered orally to patients.

Disclosed herein is a drug delivery device having a central axis, the drug delivery device comprising a carrier and an insert, the carrier comprising a first body part having a first recess; a first attachment part attached to the first body part and having a first distal end; a second body part having a second recess; an actuator mechanism configured to rotate at least one of the first body part or the second body part with respect to one another about the central axis; and an insert configured to be inserted and fixed in the second recess, the insert comprising a second attachment part and an insert body with an insert recess, the second attachment part having a second distal end.

Also disclosed herein is a carrier for a drug delivery device comprising an insert and the carrier, the carrier comprising a first body part having a first recess; a first attachment part attached to the first body part and having a first distal end; a second body part having a second recess, the second recess defining an opening on an outer surface of the second body part; and an actuator mechanism configured to rotate at least one of the first body part or the second body part with respect to one another about a central axis, wherein the second recess is configured to fixedly receive the insert comprising a second attachment part.

Further disclosed herein is an insert for a drug delivery device comprising a carrier and the insert, the insert comprising an insert body configured to be fixably arranged within a recess of the drug delivery device; an attachment part rotatably attached to the insert body and having a distal end; a chamber configured to accommodate an active drug substance, wherein the chamber is in fluid communication with the attachment part; and a cover element attached to the insert body and configured to at least partially cover and prevent rotation of the attachment part.

It is an important advantage of a drug delivery device that the drug delivery device can be reusable after passing through a patient's system. It is also an important advantage of the drug delivery system to be easy to assembly and/or manufacture. Additionally, it is an important advantage of the drug delivery device to provide improved delivery of an active drug substance.

The present disclosure allows for improved reusability of drug delivery devices. In particular, the drug delivery device may be a carrier able to receive an insert having a particular active drug substance. Once the drug delivery system has passed through the patient, and released the active drug substance, the insert can be easily removed from the carrier and, after any optional sterilization and/or cleaning, a new insert can be inserted back into the carrier. Alternatively, the insert may be removed, refilled, and reinserted into the carrier. The new insert can then be given back to the original patient for further use, or given to a new patient. This can further advantageously reduce waste as a significant portion of the drug delivery device can be reused.

Moreover, the present disclosure allows for improved assembly of drug delivery devices. In particular, the carrier and insert can be manufactured separately, and then easily combined into the drug delivery device. Further, either the carrier or the insert can be modified as required, allowing for a modular approach to a drug delivery system. Thus, the insert can be used with multiple types of carriers, and vice versa.

Further, the present disclosure allows for improved active drug substance delivery in a drug delivery device. For example, the drug delivery device can include a releasable spike containing the active drug substance. Thus, the spike can remain in the patient while the remainder of the drug delivery device leaves the patient. This can improve active drug substance delivery, while also speeding up retrieval of the drug delivery device.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1:
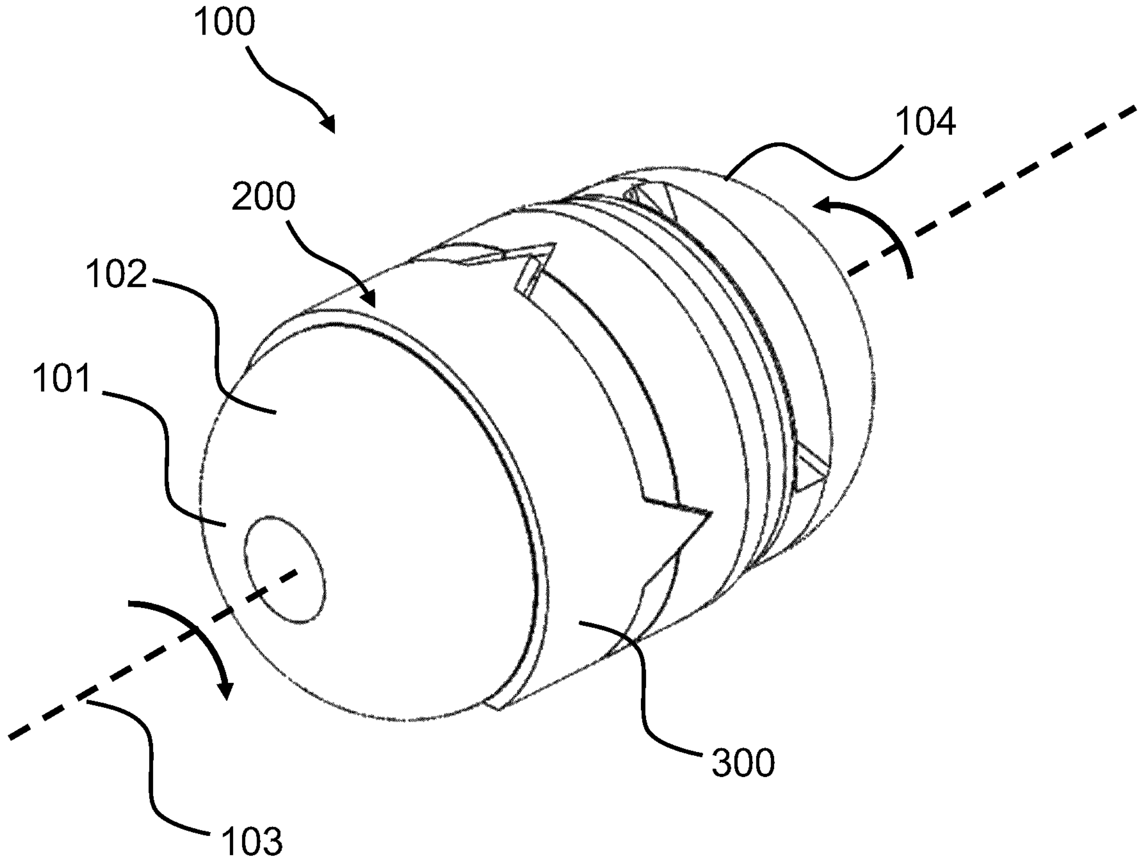
FIG. 1 shows a perspective view of an exemplary drug delivery device.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments and the functionalities associated therewith. They are not intended as an exhaustive description of the invention or as a limitation on the scope of the invention or the physical appearance of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A drug delivery device having an axis is disclosed, the drug delivery device comprising a first body part having a first recess; a first attachment part; a second body part having a second recess; an actuator mechanism configured to rotate at least one of the first body part or the second body part with respect to one another about the axis; and an insert configured to be inserted and fixed in the second recess, wherein the insert has a second attachment part and an insert body, the second attachment part having a distal end. In one or more exemplary drug delivery devices, the axis can be a central axis.

An alternative drug delivery device having an axis is disclosed, the drug delivery device comprising a first body part; a first attachment part; a second body part having a second recess; an actuator mechanism configured to rotate at least one of the first body part or the second body part with respect to one another about the axis; and an insert configured to be inserted and fixed in the second recess, wherein the insert has a second attachment part and an insert body, the second attachment part having a distal end. In one or more exemplary drug delivery devices, the axis can be a central axis.

Also disclosed herein is a carrier for a drug delivery device comprising an insert and the carrier, the carrier comprising a first body part having a first recess; a first attachment part attached to the first body part and having a first distal end; a second body part having a second recess, the second recess defining an opening on an outer surface of the second body part; and an actuator mechanism configured to rotate at least one of the first body part or the second body part with respect to one another about an axis, wherein the second recess is configured to fixedly receive the insert comprising a second attachment part. In one or more exemplary drug delivery devices, the axis can be a central axis.

Also disclosed herein is a carrier for a drug delivery device comprising a first insert, a second insert, and the carrier, the carrier comprising a first body part having a first recess, the first recess defining an opening on an outer surface of the first body part; a second body part having a second recess, the second recess defining an opening on an outer surface of the second body part; and an actuator mechanism configured to rotate at least one of the first body part or the second body part with respect to one another about an axis, wherein the first recess is configured to fixedly receive the first insert comprising a first attachment part, and wherein the second recess is configured to fixedly receive the second insert comprising a second attachment part. In one or more exemplary drug delivery devices, the axis can be a central axis.

Further disclosed herein is an insert for a drug delivery device comprising a carrier and the insert, the insert comprising an insert body configured to be fixably arranged within a recess of the drug delivery device; an attachment part rotatably attached to the insert body and having a distal end; a chamber configured to accommodate an active drug substance, wherein the chamber is in fluid communication with the attachment part; and cover element attached to the insert body and configured to at least partially cover and prevent rotation of the attachment part.

In one or more exemplary drug delivery devices, the drug delivery device may be a carrier in combination with an insert (e.g., with the insert inserted into the carrier). In one or more exemplary drug delivery devices, the drug delivery device may be a carrier. Accordingly, discussion with respect to the drug delivery device may be applicable to the carrier, and vice versa.

The drug delivery device may have a size and geometry designed to fit into a pharmaceutical composition for oral administration.

The drug delivery device/pharmaceutical composition may be configured to be taken into the body via the oral orifice. Thus, the outer dimensions of the drug delivery device/pharmaceutical composition may be small enough for a user to swallow. The drug delivery device may be adapted to carry a drug substance (e.g., an active drug substance) into the body of the user, via the digestive system, so that the drug delivery device may e.g., travel from the mouth of the user into the stomach, via the oesophagus. The drug delivery device may further travel into the intestines from the stomach, and may optionally travel into the bowels and out through the rectum.

The drug delivery device may be configured to deliver the drug in any part of the digestive system of the user, where in one example it may be configured to deliver a drug substance into the stomach of the user. In another example, the drug delivery device may be adapted to initiate the drug delivery when the device has passed the stomach and has entered the intestine of the user. In other words, the drug delivery device may be configured to attach to a wall of the stomach or a wall of the intestines, e.g., depending on the desired release position of the active drug substance.

The attachment part(s) of the drug delivery device may be configured to interact with the inner surface linings of the gastrointestinal tract, so that the drug delivery device may e.g., be attached to the inner surface (mucous membrane) of the stomach, or alternatively to the mucous membrane of the intestines. The attachment part(s) may be configured to interact with the mucous membranes, e.g., in order to fix or attach the drug delivery device, e.g., for a period of time, inside the body of the user. By attaching the drug delivery device, it will allow a drug substance to be delivered into a part of the digestive system, in order to provide a drug substance to the body of the user. The attachment part(s) may be configured to interact with the mucous membranes, e.g., in order to inject drug substance into the gastrointestinal tract wall. In one or more exemplary drug delivery devices, the attachment part(s) may remain in the linings to provide the drug substance while a remainder of the drug delivery device is released.

The drug delivery device has an axis optionally extending from a first end to a second end of the drug delivery device. The axis may be a central axis. The axis may be an off-center axis. The drug delivery device may have a length (e.g. largest extension from first end to second end along central axis), in the range from 3 mm to 35 mm, such as in the range from 5 mm to 26 mm. The drug delivery device may be elongated. The drug delivery device may be capsule shaped. The drug delivery device may have a capsule-like shape.

In one or more drug delivery devices, the drug delivery device may be located within a capsule, e.g. oral composition. For example, the capsule could be a gel capsule, but the particular material is not limiting. The capsule could further contain a filler, for example lactose or dissolvable powder, along with the drug delivery device.

In one or more exemplary drug delivery devices, the drug delivery device may have a coating, such as a spray, for ease of swallowing.

The drug delivery device may have a width and/or height (e.g. largest extensions along width axis and height axis, respectively) in the range from 1 mm to 20 mm. Height and width are the largest extensions of the drug delivery device perpendicular to the central axis.

In one or more exemplary drug delivery devices, the dimensions of the drug delivery device, at least in an initial state or first state prior to actuation of the first attachment part and/or the second attachment part, may be represented by a length (largest extension along central axis), a width (largest extension along width axis perpendicular to the central axis) and a height (largest extension along height axis perpendicular to the central axis and the width axis). The height of the drug delivery device may be in the range from 1 mm to 15 mm. The width of the drug delivery device may be in the range from 1 mm to 15 mm.

In one or more exemplary drug delivery devices, the drug delivery device may be constructed in a way that secures the drug delivery part to deliver a payload or active drug substance into the internal tissue or internal surface for distribution of the active drug substance in the subject through the blood vessels.

The carrier comprises a first body part. The first body part may be a one-part body part, e.g., unitary. The first body part may be a two-part body part, i.e. the first body part may comprise a first primary body part and a first secondary body part. The first body part has an outer surface. A first recess may be formed in the outer surface of the first body part. Alternatively, a first primary recess and/or a first secondary recess may be formed in the outer surface of the first body part.

The carrier comprises a first attachment part. The first attachment part may comprise a first base part and/or a first spike, e.g. needle. The first attachment part has a first proximal end and a first distal end. The first attachment part, such as the first spike, optionally has or extends along a first attachment axis. A first tip of the first spike forms the first distal end. In other words, the first distal end is a first tip of the first spike. The first base may be arranged at or constitute the first proximal end of the first attachment part. The first spike may have a length in the range from 1 mm to 15 mm such, as in the range from 3 mm to 10 mm. Thereby sufficient penetration into the internal tissue may be provided for while at the same time reducing the risk of damaging the internal tissue. The first distal end of the first attachment part may be provided with a tip configured to penetrate a biological tissue. The first distal end of the first attachment part may be provided with a gripping part configured to grip a biological tissue.

The first spike may have a cross-sectional diameter in the range from 0.1 mm to 5 mm, such as in the range from 0.5 mm to 2.0 mm.

The first spike may be straight and/or curved. The first spike may comprise a first primary section that is straight. The first spike may comprise a first secondary section, e.g. between the first primary section and the first distal end or between the first base and the first primary section. The first secondary section may be curved.

The first spike may include two or more straight portions formed at an angle. For example, the first spike may have a proximal portion that extends at a first angle from a connection point to the drug delivery device and a distal portion that extends at a second angle from a connection point to the drug delivery device. The first angle and the second angle may be different. The proximal portion may connect to the distal portion at a joint (e.g., bend, connection, angle) and have a joint angle between the proximal portion and the distal portion. The joint angle may be an acute angle, an obtuse angle, or a right angle. The angle may be, for example, 10, 20, 30, 40, 50, 60, 70, 80, 90, 100, 120, 130 140, 150, 160, or 170 degrees. This can advantageously allow for different angles of attach when the first spike interacts with inner surface linings. This may allow for improved attachment of the drug delivery device, while helping to reduce or avoid tissue damage. Further, the joint may be flexible. Alternatively, the joint may not be flexible.

The joint may be located at a center, or generally at a center, of a length of the first spike. Alternatively, the joint may be located 40, 45, 55, 60, or 65% up a length of the first spike from the proximal end.

In one or more exemplary first attachment parts, the first spike may have three, four, or five different portions at different angles, each connected by a joint. In some iterations, any or all of the different portions may be straight or curved. Each joint may be flexible or not flexible.

The attachment parts (e.g., the first attachment part and/or the second attachment part discussed below) of the carrier and/or insert and/or drug delivery device may be seen as any kind of attachment parts that may be capable of attaching the drug delivery device to a biological tissue, such as a stomach wall, a wall of the bowels and/or intestines of a human or animal body. The attachment parts may be adapted to extend in a direction away from the central axis of the drug delivery device and/or carrier, and/or a central axis of the first attachment part. This may mean that the attachment part(s), e.g., at least in an activated state or second state of the drug delivery device, may extend in a direction away from a peripheral surface (in radial direction) of the first body part and/or the second body part, so that the attachment part extends farther in a radial direction than the peripheral or outer surface of the body part.

Advantageously, the drug delivery device may be attached, and may deliver the active drug substance, to a particular location in a patient's intestinal wall. Of course, the delivery device may be attached, and may deliver the active drug substance, to other places as well. In one or more exemplary drug delivery devices, the drug delivery device, such as the spike, may penetrate the muscularis mucosa. In one or more exemplary drug delivery devices, the drug delivery device, such as the spike, may not penetrate the muscularis externa. In one or more exemplary drug delivery devices, the spike may be positioned in the submucosa. In one or more exemplary drug delivery devices, the spike may be positioned in the submucosa parallel to the gut wall.

The first attachment part may be fixed or rotationally attached to the first body part.

In one or more exemplary drug delivery devices, the carrier comprises a second body part. The second body part may be a two-part body part, i.e. the second body part may comprise a second primary body part and a second secondary body part. The second body part can be configured to receive the insert.

In one or more exemplary drug delivery devices, the drug delivery device may include an insert (e.g., removable insert, module, removable module, component, removable component, housing, removable housing) that can be inserted into the carrier to form the drug delivery device. In one or more exemplary drug delivery devices, the drug delivery device may include a plurality of inserts (e.g., removable inserts, modules, removable modules, components, removable components, housings, removable housings) that can each be inserted into the carrier to form the drug delivery device.

In one or more exemplary drug delivery devices, the insert may have a longitudinal length of 2.6, 2.7, 2.8, 2.9, 3.0, 3.1, 3.2, 3.3, 3.4, 3.5, or 3.5 mm. In one or more exemplary drug delivery devices, the insert may have a longitudinal length of greater than 2.6, 2.7, 2.8, 2.9, 3.0, 3.1, 3.2, 3.3, 3.4, 3.5, or 3.5 mm. In one or more exemplary drug delivery devices, the insert may have a longitudinal length of less than 2.6, 2.7, 2.8, 2.9, 3.0, 3.1, 3.2, 3.3, 3.4, 3.5, or 3.5 mm.

In one or more exemplary drug delivery devices, the insert may have a longitudinal length of 2, 3, 4, 5, 6, 7, 8, 9, 10, 11, 12, 13, 14, or 15 mm. In one or more exemplary drug delivery devices, the insert may have a longitudinal length of greater than 2, 3, 4, 5, 6, 7, 8, 9, 10, 11, 12, 13, 14, or 15 mm. In one or more exemplary drug delivery devices, the insert may have a longitudinal length of less than 2, 3, 4, 5, 6, 7, 8, 9, 10, 11, 12, 13, 14, or 15 mm.

In one or more exemplary drug delivery devices, the insert may have a radius of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the insert may have a radius of less than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the insert may have a radius of greater than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm.

For example, the insert can be inserted into the first body part and/or the second body part, such as in a recess (e.g., gap, cavity, slot, hole, aperture, retainer, first recess, second recess). In one or more exemplary drug delivery devices, the insert can be inserted into the first body part. In one or more exemplary drug delivery devices, the insert can be inserted into the second body part.

In one or more exemplary drug delivery devices, a first insert can be inserted into the first body part and a second insert can be inserted into the second body part. The first insert can be identical to the second insert. The first insert can be different from the second insert. The first insert can be structurally the same as the second insert, but contain different active substances. In one or more exemplary drug delivery systems only one of the first insert and the second insert may contain an active substance.

The insert (e.g., the first insert and/or the second insert) may include one or more of the components discussed herein, such as a second attachment part. The second attachment part may be fixed or rotationally attached to the insert. In one or more exemplary drug delivery devices, the insert has an outer surface. Thus, when inserted into the carrier, the insert can form an outer surface of the carrier and thus the drug delivery device. An insert recess may be formed in the outer surface of the insert, as discussed in detail below. The insert recess may advantageously be sterilized.

In one or more exemplary drug delivery devices, the insert recess can have a longitudinal length of 1.1, 1.2, 1.3, 1.4, 1.5, 1.6, 1.7, 1.8, 1.9, 2.0, or 2.1 mm. In one or more exemplary drug delivery devices, the insert recess can have a longitudinal length of greater than 1.1, 1.2, 1.3, 1.4, 1.5, 1.6, 1.7, 1.8, 1.9, 2.0, or 2.1 mm. In one or more exemplary drug delivery devices, the insert recess can have a longitudinal length of less than 1.1, 1.2, 1.3, 1.4, 1.5, 1.6, 1.7, 1.8, 1.9, 2.0, or 2.1 mm.

In one or more exemplary drug delivery devices, the insert recess may have a longitudinal length of 2.6, 2.7, 2.8, 2.9, 3.0, 3.1, 3.2, 3.3, 3.4, 3.5, or 3.5 mm. In one or more exemplary drug delivery devices, the insert recess may have a longitudinal length of greater than 2.6, 2.7, 2.8, 2.9, 3.0, 3.1, 3.2, 3.3, 3.4, 3.5, or 3.5 mm. In one or more exemplary drug delivery devices, the insert recess may have a longitudinal length of less than 2.6, 2.7, 2.8, 2.9, 3.0, 3.1, 3.2, 3.3, 3.4, 3.5, or 3.5 mm.

In one or more exemplary drug delivery devices, the insert recess may have a longitudinal length of 2, 3, 4, 5, 6, 7, 8, 9, 10, 11, 12, 13, 14, or 15 mm. In one or more exemplary drug delivery devices, the insert recess may have a longitudinal length of greater than 2, 3, 4, 5, 6, 7, 8, 9, 10, 11, 12, 13, 14, or 15 mm. In one or more exemplary drug delivery devices, the insert recess may have a longitudinal length of less than 2, 3, 4, 5, 6, 7, 8, 9, 10, 11, 12, 13, 14, or 15 mm.

In one or more exemplary drug delivery devices, the insert recess may have a radius of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the insert recess may have a radius of less than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the insert recess may have a radius of greater than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm.

In one or more exemplary drug delivery devices, the insert may include a second attachment part having a chamber (e.g., cavity, receptacle) for holding an active drug substance, as discussed in detail below. In one or more exemplary drug delivery devices, the chamber can be located in the second spike. Accordingly, the chamber may be in fluid communication with a distal end of the second attachment part. Thus, the active drug substance can be released from the second attachment part, and thus from the drug delivery device.

In one or more exemplary drug delivery devices, the carrier can include an actuator mechanism. The actuator mechanism is configured to rotate the first body part in relation to the second body part, and thus the inserted insert, about a primary axis of the drug delivery device. The primary axis may be parallel to and/or coinciding with the central axis.

In one or more exemplary drug delivery devices, the first body part is configured to rotate in a first direction and/or the second body part is configured to rotate in a second direction opposite to the first direction.

The drug delivery device may comprise a frame part, where different parts, such as the first body part and/or the second body part are attached, e.g., fixed or rotatably attached to the frame part. In one or more exemplary drug delivery devices, the actuator mechanism, or parts thereof, may be attached to the frame part. Thereby, separate rotation of the first body part and the second body part in relation to the frame part may be provided for.

The rotational connection between the first body part and the second body part allows the first body part to rotate relative to the second body part and the insert, without the two parts separating from each other before the attachment part(s) interact with the internal tissue, such as mucous membranes. Such a connection may be obtained in a plurality of ways, where in one example the first body part has a plug connection and the second body part has a socket connection, where this plug and socket configuration allows the first body part to rotate relative to the second body part. A second example could be to provide an axle that may be coaxial with the central axis and/or the primary axis, where the first body part and the second body part, and optionally the insert, are configured to receive the axle, and a stopping device is arranged at first and second ends of the axle, on each side of the combined first and second body part, preventing the first body part and the second body part to slide in a longitudinal direction along the axle. The axle may be integrated in the first body part or in the second body part.

The first and/or the second body part may be arranged to rotate freely relative to each other, e.g., at least in the second state, and thereby allowing the attachment parts to rotate relative to each other. Thus, the attachment parts may be adapted to come into contact and/or penetrate tissue of the gastrointestinal tract. The rotation of the body parts relative to each other using a resilient force may move the attachment parts in such a way that they are capable of e.g., penetrating or pinching the mucous membrane in order to fix the drug delivery device at a location in the gastrointestinal tract, such as the stomach or intestines. The penetrating and/or pinching force may come from the actuator mechanism/resilient part, where the resilient part may be adapted to store a resilient force that is capable of forcing the attachment parts towards each other when the resilient force of the resilient part has been at least partly unleashed. The resilient part may e.g., be in the form of a spring or spring element, for example a torsional spring or a power spring, where the spring may be wound up to store mechanical energy, where the mechanical energy may be transmitted to the first and/or the second body part. When the mechanical energy is released, the first body part may rotate relative to the second body part, and where the mechanical energy may be transferred into the attachment parts via the body parts.

Within the context of the present description the term “rotational force” may be seen as torque, moment, moment of force, rotational force or “turning effect”. Another definition of the term “rotational force” may be the product of the magnitude of the force and the perpendicular distance of the line of action of force from the axis of rotation. The rotational force may be seen as the force which is transferred from the resilient part to the attachment members of the drug delivery device via the body parts.

The rotational force may be defined as being large enough to penetrate into the gastrointestinal tissue. When the rotational force is applied to both the first and the second body part, the first attachment member may come into contact with the surface to be attached to, and where the rotational force applied to the second body part may cause the second attachment part to come into contact with the same surface, where the first attachment part provides a force, while the second attachment part provides a counter force to the first attachment part, so that the force is applied in such a manner that the first attachment part is forced in a direction towards the second attachment part on the insert, or vice versa.

In one or more exemplary drug delivery devices, a distance between the first attachment axis of the first attachment part and the primary axis, e.g., at least in an activated state or second state of the drug delivery device and optionally in an initial state of the drug delivery device, is larger than 0.5 mm.

In one or more exemplary drug delivery devices, a distance between the second attachment axis of the second attachment part and the primary axis, e.g., at least in an activated state or second state of the drug delivery device and optionally in an initial state of the drug delivery device, is larger than 0.5 mm.

In one or more exemplary drug delivery devices, the first attachment part is rotationally attached to the first body part, e.g. via a first joint connection having a first rotation axis. In other words, the first attachment part is optionally configured to rotate about a first rotation axis, e.g. in relation to the first body part. The first rotation axis may be parallel to the central axis and/or the primary axis. The first rotation axis may form a first angle with the central axis and/or the primary axis. The first angle may be less than 15°. The first angle may be in the range from 75° to 105°, such as 90°±5° or 90°.

In one or more exemplary drug delivery devices, the first body part may define a first recess (e.g., cavity, gap, slot, hole, aperture, retainer, first body recess) extending to an outer surface of the first body part. The recess may be formed by solid walls on all sides except an outermost surface, which is open. For example, the recess may be formed by a first wall, a second wall, and a bottom. The first wall may be opposite the second wall. The bottom may connect the first wall and the second wall. In one or more exemplary drug delivery devices, the first wall and/or the bottom wall and/or the second wall are flat. In one or more exemplary drug delivery devices, the first wall and/or the bottom wall and/or the second wall are curved. The open outermost surface may be curved to follow along with an outer surface of the carrier.

The first attachment part may be rotationally connected within the first recess. For example, the first attachment part may be rotationally connected within the first recess along a first attachment part axis. The first attachment part axis may be, for example, a pin (e.g., arm, support). The first attachment part axis may be aligned with the central axis and/or the primary axis. The first attachment part axis may be parallel to the central axis and/or the primary axis. The first attachment part axis may be angled with respect to the central axis and/or the primary axis. Accordingly, the first attachment part can rotate within the recess along the first attachment part axis. Further, rotation of the first attachment part may be stopped at end surfaces of the recess.

The first recess may extend along a portion of the outer surface of the first body. The first recess may extend fully along an outer circumference of the first body. The first recess may extend around 10, 15, 20, 25, 30, 35, 40, 45, 50, 55, 60, 65, 70, 75, 80, 85, 90, 95, or 100% of an outer circumference of the first body. The first recess may extend around greater than 10, 15, 20, 25, 30, 35, 40, 45, 50, 55, 60, 65, 70, 75, 80, 85, 90, or 95% of an outer circumference of the first body. The first recess may extend around less than 10, 15, 20, 25, 30, 35, 40, 45, 50, 55, 60, 65, 70, 75, 80, 85, 90, 95, or 100% of an outer circumference of the first body. The first body may optionally contain more than one first recess, for example of a plurality of first attachment parts are used on the first body. If more than one first recess is used, they may be spaced longitudinally apart and/or circumferentially apart.

The first recess may extend from an outer surface toward the central axis through 5, 10, 15, 20, 25, 30, 35, or 40% of the drug delivery device. The first recess may extend from an outer surface toward the central axis through greater than 5, 10, 15, 20, 25, 30, 35, or 40% of the drug delivery device. The first recess may extend from an outer surface toward the central axis through less than 5, 10, 15, 20, 25, 30, 35, or 40% of the drug delivery device.

In one or more exemplary drug delivery devices, the first recess may extend circumferentially, or partially circumferentially around the first body with the central axis being the longitudinal direction. The first recess may extend perpendicularly with respect to the central axis and/or the primary access (e.g., may extend along a cross section of the drug delivery device perpendicular to the central axis and/or the primary access).

The first recess may have any number of shapes when viewed in cross section with respect to the first attachment part axis. For example, the first recess can be a portion of a circle, such as a half circle. The first recess can be a triangle. The first recess can be a sector of a circle. The first recess can be generally circular in shape, with a portion of the circle cut off. For example, the portion of the circle can be cut off from two points on the circumference of the circle connected by a single straight line. The first recess can be a curved edge connected by two straight edge. The first recess can be two curved edges connected to each other by two straight edges.

For example, in one or more exemplary drug delivery systems, the first recess can form a slice of the first body part. Thus, the first recess can extend greater circumferentially than longitudinally.

In alternate drug delivery devices, the first recess is a cylinder. In alternate drug delivery devices, the first recess is a rectangular prism.

The first recess may be relatively thin. For example, the first recess may be the longitudinal length of the first spike. The first recess may have a longitudinal length slightly longer than the first spike.

In one or more exemplary drug delivery devices, the first recess can have a longitudinal length of 1.1, 1.2, 1.3, 1.4, 1.5, 1.6, 1.7, 1.8, 1.9, 2.0, or 2.1 mm. In one or more exemplary drug delivery devices, the first recess can have a longitudinal length of greater than 1.1, 1.2, 1.3, 1.4, 1.5, 1.6, 1.7, 1.8, 1.9, 2.0, or 2.1 mm. In one or more exemplary drug delivery devices, the first recess can have a longitudinal length of less than 1.1, 1.2, 1.3, 1.4, 1.5, 1.6, 1.7, 1.8, 1.9, 2.0, or 2.1 mm.

In one or more exemplary drug delivery devices, the first recess may have a longitudinal length of 2.6, 2.7, 2.8, 2.9, 3.0, 3.1, 3.2, 3.3, 3.4, 3.5, or 3.5 mm. In one or more exemplary drug delivery devices, the first recess may have a longitudinal length of greater than 2.6, 2.7, 2.8, 2.9, 3.0, 3.1, 3.2, 3.3, 3.4, 3.5, or 3.5 mm. In one or more exemplary drug delivery devices, the first recess may have a longitudinal length of less than 2.6, 2.7, 2.8, 2.9, 3.0, 3.1, 3.2, 3.3, 3.4, 3.5, or 3.5 mm.

In one or more exemplary drug delivery devices, the first recess may have a longitudinal length of 2, 3, 4, 5, 6, 7, 8, 9, 10, 11, 12, 13, 14, or 15 mm. In one or more exemplary drug delivery devices, the first recess may have a longitudinal length of greater than 2, 3, 4, 5, 6, 7, 8, 9, 10, 11, 12, 13, 14, or 15 mm. In one or more exemplary drug delivery devices, the first recess may have a longitudinal length of less than 2, 3, 4, 5, 6, 7, 8, 9, 10, 11, 12, 13, 14, or 15 mm.

In one or more exemplary drug delivery devices, the first recess may have a radius of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the first recess may have a radius of less than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the first recess may have a radius of greater than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm.

The first recess may be parallel to the central axis and/or the primary access. The first recess may be orthogonal to the central axis and/or the primary access. In one or more exemplary drug delivery devices, the first recess extends perpendicular to the central axis. The first recess may be at an angle of 5, 10, 15, 20, 25, 30, 35, 40, 45, 50, 55, 60, 65, 70, 75, 80, or 85 degrees with respect to the central axis and/or the primary access. The first recess may be at an angle of greater than 5, 10, 15, 20, 25, 30, 35, 40, 45, 50, 55, 60, 65, 70, 75, 80, or 85 degrees with respect to the central axis and/or the primary access. The first recess may be at an angle of less than 5, 10, 15, 20, 25, 30, 35, 40, 45, 50, 55, 60, 65, 70, 75, 80, or 85 degrees with respect to the central axis and/or the primary access.

The first body attachment part axis may be parallel to the central axis and/or the primary access. The first body attachment part axis may be orthogonal to the central axis and/or the primary access. The first body attachment part axis may be at an angle of 5, 10, 15, 20, 25, 30, 35, 40, 45, 50, 55, 60, 65, 70, 75, 80, or 85 degrees with respect to the central axis and/or the primary access. The first body attachment part axis may be at an angle of greater than 5, 10, 15, 20, 25, 30, 35, 40, 45, 50, 55, 60, 65, 70, 75, 80, or 85 degrees with respect to the central axis and/or the primary access. The first body attachment part axis may be at an angle of less than 5, 10, 15, 20, 25, 30, 35, 40, 45, 50, 55, 60, 65, 70, 75, 80, or 85 degrees with respect to the central axis and/or the primary access.

Thus, the first attachment part may rotate on the first attachment part axis in order to move perpendicular to the central axis and/or the primary axis. In certain embodiments, the first attachment part may rotate at an angle between perpendicular and parallel with respect to the central axis and/or the primary axis.

In one or more exemplary drug delivery devices, when the first body part and/or the second body part rotate with respect to one another, the first attachment part and/or the second attachment part can rotate out of their respective recesses (e.g., first recess and insert recess) due to the rotation of the first body part and/or the second body part. The continued rotation of the first body part and/or the second body part then causes the first attachment part and/or the second attachment part to pierce tissue to hold the drug delivery device in place. Thus, in a first state, the first attachment part may be located within the first recess. After rotation to a second state, the first attachment part may be located at least partially outside of the first recess.

In one or more exemplary drug delivery devices, the first attachment part includes a first arm. In one or more exemplary drug delivery devices, the first attachment part includes a first spike. The first spike can be attached at a distal end of the first arm. The first spike can be mechanically attached to the distal end of the first arm. The first spike can be chemically attached to the distal end of the first arm. The first spike can be integral with the first arm. The first spike can be permanently attached to the distal end of the first arm. The first spike can rotate with respect to the first arm, such as on an axis at the distal end of the first arm. The first spike may not rotate with respect to the first arm. The first spike can be removably attached to the distal end of the first arm. A proximal end of the first arm can be associated with the first attachment part axis. Thus, the first arm and first spike can rotate with respect to the first attachment part axis.

The first arm may be straight. The first arm may be bent. The first arm may include a number of bends. The first arm may be curved. The first arm can be a single unit. The first arm can be a number of segments attached together. The number of segments may be rigidly attached together. The number of segments may be rotatably attached.

The first arm attachment part can optionally include further intermediate components. For example, the first arm may include a cradle for retaining the first spike. The first arm may include a holder for retaining the first spike.

In one or more exemplary drug delivery devices, the first attachment part extends, e.g. at least in an activated state of the drug delivery device and optionally in an initial state of the drug delivery device, in a direction away from the first body part. In other words, the first spike may extend, e.g. at least in an activated state of the drug delivery device and optionally in an initial state, from an outer surface of the first body part. Formulated differently, the first attachment axis may, e.g. at least in an activated state of the drug delivery device and optionally in an initial state of the drug delivery device form an angle of at least 45° with the central axis and/or the primary axis. An attachment part extending in a direction is to be understood as the direction from proximal end of attachment part/spike part to distal end of attachment part along the attachment axis of the attachment part.

The first attachment part may in a first state of the drug delivery device extend in a first primary direction and in a second state of the drug delivery device extend in a first secondary direction. The first primary direction and the first secondary direction may form an angle of at least 30°. The first primary direction may be parallel or substantially parallel to the central axis. The first primary direction may form an angle less than 60° with the central axis. The first secondary direction may form an angle of at least 60° such as about 90° with the central axis. The first secondary direction may be perpendicular to the central axis.

The first distal end of the first attachment part may be configured to move or be moved from a first primary position in a first state of the drug delivery device to a first secondary position in the second state.

The drug delivery device comprises a second attachment part located on the second body part and/or the insert. The second attachment part may comprise a second base part and/or a second spike. The second attachment part has a second proximal end and a second distal end. The second attachment part, such as the second spike, optionally has or extends along a second attachment axis. A second tip of the second spike forms the second distal end. In other words, the second distal end is a second tip of the second spike. The second base may be arranged at or constitute the second proximal end of the second attachment part. The second spike may have a length in the range from 1 mm to 15 mm such, as in the range from 3 mm to 10 mm. Thereby sufficient penetration into the internal tissue may be provided for while at the same time reducing the risk of damaging the internal tissue. The second distal end of the second attachment part may be provided with a tip configured to penetrate a biological tissue. The second distal end of the second attachment part may be provided with a gripping part configured to grip a biological tissue.

The second spike may have a cross-sectional diameter in the range from 0.1 mm to 5 mm, such as in the range from 0.5 mm to 2.0 mm.

The second spike may be straight and/or curved. The second spike may comprise a second primary section that is straight. The second spike may comprise a second secondary section, e.g. between the second primary section and the second distal end or between the second base and the second primary section. The second secondary section may be curved.

Alternatively, the second spike may include two or more straight portions formed at an angle. For example, the second spike may have a proximal portion that extends at a first angle from a connection point to the drug delivery device and a distal portion that extends at a second angle from a connection point to the drug delivery device. The first angle and the second angle may be different. The proximal portion may connect to the distal portion at a joint (e.g., bend, connection, angle) and have a joint angle between the proximal portion and the distal portion. The joint angle may be an acute angle, an obtuse angle, or a right angle. The angle may be, for example, 10, 20, 30, 40, 50, 60, 70, 80, 90, 100, 120, 130 140, 150, 160, or 170 degrees. This can advantageously allow for different angles of attach when the first spike interacts with inner surface linings. This may allow for improved attachment of the drug delivery device, while helping to reduce or avoid tissue damage. Further, the joint may be flexible. Alternatively, the joint may not be flexible.

The joint may be located at a center, or generally at a center, of a length of the second spike. Alternatively, the joint may be located 40, 45, 55, 60, or 65% up a length of the second spike from the proximal end.

In alternative embodiments, the second spike may have three, four, or five different portions at different angles, each connected by a joint. In some iterations, any or all of the different portions may be straight or curved. Each joint may be flexible or not flexible.

In one or more exemplary drug delivery devices, both the first second and the second spike include a joint. However, only one of the first spike and the second spike may include a joint with the other being straight and/or curved. If both the first spike and the second spike include a joint, the first distal tip and the second distal tip may be angled towards one another in order to facilitate attachment when the first body part and the second body part rotate with respect to one another.

In one or more exemplary drug delivery devices, the second attachment part is rotationally attached to the insert, e.g. via a second joint connection having a second rotation axis. In one or more exemplary drug delivery devices, the second attachment part is rotationally attached within an insert recess of the insert. In other words, the second attachment part is optionally configured to rotate about a second rotation axis (or second attachment part axis), e.g. in relation to the removable insert, and thus the second body part. The second rotation axis may be parallel to the central axis and/or the primary axis. The second rotation axis may form a second angle with the central axis and/or the primary axis. The second angle may be less than 15°. The second angle may be in the range from 75° to 105°, such as 90°±5° or 90°.

In one or more exemplary drug delivery devices, the insert may define an insert recess (e.g., cavity, gap, slot, hole, aperture, retainer, second recess) extending to an outer surface of the insert (and thus the second body part when the insert is in the carrier). The insert recess may be formed by solid walls on all sides except an outermost surface which is open. For example, the insert recess may be formed by a first wall, a second wall, and a bottom. The first wall may be opposite the second wall. The bottom may connect the first wall and the second wall. In one or more exemplary drug delivery devices, the first wall and/or the bottom wall and/or the second wall are flat. In one or more exemplary drug delivery devices, the first wall and/or the bottom wall and/or the second wall are curved. The open outermost surface may be curved to follow along with an outer surface of the carrier and/or the insert.

The second attachment part may be rotationally connected within the insert recess. For example, the second attachment part may be rotationally connected within the insert recess along a second attachment part axis. The second attachment part axis may be, for example, a pin (e.g., arm, support). The second attachment part axis may be aligned with the central axis and/or the primary axis. The second attachment part axis may be parallel to the central axis and/or the primary axis. The second attachment part axis may be angled with respect to the central axis and/or the primary axis. Accordingly, the second attachment part can rotate within the recess along the second attachment part axis. Further, rotation of the second attachment part may be stopped at end surfaces of the recess.

The insert recess may extend along a portion of the outer surface of the second body. The insert recess may extend fully along an outer circumference of the insert. The insert recess may extend around 10, 15, 20, 25, 30, 35, 40, 45, 50, 55, 60, 65, 70, 75, 80, 85, 90, 95, or 100% of an outer circumference of the insert. The insert recess may extend around greater than 10, 15, 20, 25, 30, 35, 40, 45, 50, 55, 60, 65, 70, 75, 80, 85, 90, or 95% of an outer circumference of the insert. The insert recess may extend around less than 10, 15, 20, 25, 30, 35, 40, 45, 50, 55, 60, 65, 70, 75, 80, 85, 90, 95, or 100% of an outer circumference of the insert. The insert may optionally contain more than one insert body recess, for example of a plurality of second attachment parts are used on the insert. If more than one insert recess is used, they may be spaced longitudinally apart and/or circumferentially apart.

The insert recess may extend from an outer surface toward the central axis through 5, 10, 15, 20, 25, 30, 35, or 40% of the drug delivery device. The insert recess may extend from an outer surface toward the central axis through greater than 5, 10, 15, 20, 25, 30, 35, or 40% of the drug delivery device. The insert recess may extend from an outer surface toward the central axis through less than 5, 10, 15, 20, 25, 30, 35, or 40% of the drug delivery device.

In one or more exemplary drug delivery devices, the insert recess may extend circumferentially, or partially circumferentially around the first body with the central axis being the longitudinal direction. The insert recess may extend perpendicularly with respect to the central axis and/or the primary access (e.g., may extend along a cross section of the drug delivery device perpendicular to the central axis and/or the primary access).

The insert recess may have any number of shapes when viewed in cross section with respect to the second attachment part axis. For example, the insert recess can be a portion of a circle, such as a half circle. The insert recess can be a triangle. The insert recess can be a sector of a circle. The insert recess can be generally circular in shape, with a portion of the circle cut off. For example, the portion of the circle can be cut off from two points on the circumference of the circle connected by a single straight line. The insert recess can be a curved edge connected by two straight edge. The insert recess can be two curved edges connected to each other by two straight edges.

For example, in one or more exemplary drug delivery systems, the insert recess can form a slice of the insert. Thus, the insert recess can extend greater circumferentially than longitudinally.

In alternate drug delivery devices, the insert recess is a cylinder. In alternate drug delivery devices, the insert recess is a rectangular prism.

The insert recess may be relatively thin. For example, the insert recess may be the longitudinal length of the second spike. The insert recess may have a longitudinal length slightly longer than the second spike.

The insert recess may be parallel to the central axis and/or the primary access. The insert recess may be orthogonal to the central axis and/or the primary access. The insert recess may be at an angle of 5, 10, 15, 20, 25, 30, 35, 40, 45, 50, 55, 60, 65, 70, 75, 80, or 85 degrees with respect to the central axis and/or the primary access. The insert recess may be at an angle of greater than 5, 10, 15, 20, 25, 30, 35, 40, 45, 50, 55, 60, 65, 70, 75, 80, or 85 degrees with respect to the central axis and/or the primary access. The insert recess may be at an angle of less than 5, 10, 15, 20, 25, 30, 35, 40, 45, 50, 55, 60, 65, 70, 75, 80, or 85 degrees with respect to the central axis and/or the primary access.

The second body attachment part axis may be parallel to the central axis and/or the primary access. The second body attachment part axis may be orthogonal to the central axis and/or the primary access. The second body attachment part axis may be at an angle of 5, 10, 15, 20, 25, 30, 35, 40, 45, 50, 55, 60, 65, 70, 75, 80, or 85 degrees with respect to the central axis and/or the primary access. The second body attachment part axis may be at an angle of greater than 5, 10, 15, 20, 25, 30, 35, 40, 45, 50, 55, 60, 65, 70, 75, 80, or 85 degrees with respect to the central axis and/or the primary access. The second body attachment part axis may be at an angle of less than 5, 10, 15, 20, 25, 30, 35, 40, 45, 50, 55, 60, 65, 70, 75, 80, or 85 degrees with respect to the central axis and/or the primary access.

Thus, the second attachment part may rotate on the second attachment part axis in order to move perpendicular to the central axis and/or the primary axis. In certain embodiments, the second attachment part may rotate at an angle between perpendicular and parallel with respect to the central axis and/or the primary axis.

In one or more exemplary drug delivery devices, when the first body part and/or the second body part rotate with respect to one another, the first attachment part and/or the second attachment part can rotate out of their respective recesses (e.g., first recess and insert recess) due to the rotation of the first body part and/or the second body part. The continued rotation of the first body part and/or the second body part then causes the first attachment part and/or the second attachment part to pierce tissue to hold the drug delivery device in place. Thus, in a first state, the second attachment part may be located within the insert recess. After rotation to a second state, the second attachment part may be located at least partially outside of the insert recess.

In one or more exemplary drug delivery devices, the second attachment part includes a second arm. In one or more exemplary drug delivery devices, second first attachment part includes a second spike. The second spike can be attached at a distal end of the second arm. The second spike can be mechanically attached to the distal end of the second arm.

The second spike can be chemically attached to the distal end of the second arm. The second spike can be integral with the second arm. The second spike can be permanently attached to the distal end of the second arm. The second spike can rotate with respect to the second arm, such as on an axis at the distal end of the second arm. The second spike may not rotate with respect to the second arm. The second spike can be removably attached to the distal end of the second arm. A proximal end of the second arm can be associated with the second attachment part axis. Thus, the second arm and second spike can rotate with respect to the second attachment part axis.

The second arm may be straight. The second arm may be bent. The second arm may include a number of bends. The second arm may be curved. The second arm can be a single unit. The second arm can be a number of segments attached together. The number of segments may be rigidly attached together. The number of segments may be rotatably attached.

The second arm attachment part can optionally include further intermediate components.

In one or more exemplary drug delivery devices, the second attachment part includes a second (e.g., arm). In one or more exemplary drug delivery devices includes a second spike (e.g., spike). The spike can be attached at a distal end of the arm. The spike can be mechanically attached to the distal end of the arm. The spike can be chemically attached to the distal end of the arm. The spike can be integral with the arm. The spike can be permanently attached to the distal end of the arm. The spike can be removably attached to the distal end of the arm.

In one or more exemplary drug delivery devices, the second arm can include a spike holder. The spike holder can be located on the second arm distal end. The second spike can be attached to the spike holder.

In one or more exemplary drug delivery devices, the spike holder can be a cylinder. The spike holder may have an aperture (e.g., hole, lumen, bore, through hole) extend through a length (such as a longitudinal length) of the spike holder. The aperture may be configured to receive and retain the second spike. Thus, the second spike can be retained within the spike holder, which can be attached to the second arm. For example, a distal end of the second arm could include a cradle (e.g., seat, holder, slot, receiver, mating element) configured to conform with the spike holder. Alternatively, a distal end of the second arm could include a cradle (e.g., seat, holder, slot, receiver, mating element) configured to conform with the second spike.

As mentioned, the second spike may contain an active drug substance. For example, the second spike may contain a chamber for holding the active drug substance. The chamber may be, for example, a through-going bore.

In one or more exemplary drug delivery devices, the second spike may be releasable from the spike holder. For example, the spike holder may be dissolvable. The spike holder can be configured to be dissolvable at a specific time period. Once the spike holder is partially or fully dissolved, the second spike can be released from a remainder of the drug delivery device. Upon release of the second spike, the remainder of the delivery system can release from the patient while the second spike remains embedded within the patient. Thus, the drug delivery device can be retrieved and the process of reusing it can begin while the second spike continues to provide an active drug substance to the patient. This can further reduce or eliminate any accidental release of the delivery system with the active drug substance from the patient.

A proximal end of the arm can be associated with the second attachment part axis. Thus, the arm and spike can rotate with respect to the second attachment part axis. Thus, the arm is rotatable within the insert recess about a second rotation axis (e.g., the second attachment part axis), wherein the insert recess is formed by two opposing sidewalls of the insert body.

In one or more exemplary drug delivery devices, the insert may not contain an insert recess. For example, the second attachment part, be it the second spike along or the arm and spike combination, may be directly attached to an outer surface of the insert.

In one or more exemplary drug delivery devices, the second attachment part extends, e.g. at least in an activated state of the drug delivery device and optionally in an initial state of the drug delivery device, in a direction optionally away from the insert and the second body part. In other words, the second spike may extend, e.g. at least in an activated state of the drug delivery device and optionally in an initial state, from an outer surface of the insert. Formulated differently, the second attachment axis may, e.g. at least in an activated state of the drug delivery device and optionally in an initial state of the drug delivery device form an angle of at least 45° with the central axis and/or the primary axis.

The second attachment part may in a first state of the drug delivery device extend in a second primary direction and in a second state of the drug delivery device extend in a second secondary direction. The second primary direction and the second secondary direction may form an angle of at least 30°. The second primary direction may be parallel or substantially parallel to the central axis. The second primary direction may form an angle less than 60° with the central axis. The second secondary direction may form an angle of at least 60°, such as about 90° with the central axis. The second secondary direction may be perpendicular to the central axis.

The second distal end of the second attachment part may be configured to move or be moved from a second primary position in a first state of the drug delivery device to a second secondary position in the second state.

In one or more exemplary drug delivery devices, the drug delivery device comprises a third attachment part. The third attachment part can be located on the first body part and/or the second body part and/or the insert. The third attachment part may comprise a third base part and/or a third spike. The third attachment part has a third proximal end and a third distal end. The third attachment part, such as the third spike, optionally has or extends along the second attachment axis or a third attachment axis. A third tip of the third spike forms the third distal end. In other words, the third distal end is a third tip of the third spike. The third base may be arranged at or constitute the third proximal end of the third attachment part. The third spike may have a length in the range from 1 mm to 15 mm such, as in the range from 3 mm to 10 mm. Thereby sufficient penetration into the internal tissue may be provided for while at the same time reducing the risk of damaging the internal tissue. The third distal end of the third attachment part may be provided with a tip configured to penetrate a biological tissue. The third distal end of the third attachment part may be provided with a gripping part configured to grip a biological tissue.

The third spike may have a cross-sectional diameter in the range from 0.1 mm to 5 mm, such as in the range from 0.5 mm to 2.0 mm.

The third spike may be straight and/or curved. The third spike may comprise a third primary section that is straight. The third spike may comprise a third secondary section, e.g. between the third primary section and the third distal end or between the third base and the third primary section. The third secondary section may be curved.

In one or more exemplary drug delivery devices, the third attachment part is rotationally attached to the first body part. For example, the third attachment part may be located next to the first attachment part. The third distal end may be directed in the same direction as the first distal end. The third distal end may be directed in the opposite direction as the first distal end. The third distal end may be directed at an angle with respect to the first distal end. The third attachment part may be on the same first rotation axis as the first attachment part. The third attachment part may have a third rotation axis, such as via a third joint connection.

In one or more exemplary drug delivery devices, the third attachment part is rotationally attached to the insert. For example, the third attachment part may be located next to the second attachment part. The third distal end may be directed in the same direction as the second distal end. The third distal end may be directed in the opposite direction as the second distal end. The third distal end may be directed at an angle with respect to the second distal end. The third attachment part may be on the same first rotation axis as the second attachment part. The third attachment part may have a third rotation axis, such as via a third joint connection.

In one or more exemplary drug delivery devices, the third attachment part is rotationally attached to the second body part. For example, the third attachment part may be located next to the second attachment part when the insert is located in the second body part. The third distal end may be directed in the same direction as the second distal end. The third distal end may be directed in the opposite direction as the second distal end. The third distal end may be directed at an angle with respect to the second distal end. The third attachment part may have a third rotation axis, such as via a third joint connection. The third rotation axis may be parallel to, or in line with, the second rotation axis.

In one or more exemplary drug delivery devices, the third attachment part is optionally configured to rotate about a third rotation axis. The third rotation axis may be parallel to the central axis and/or the primary axis. The third rotation axis may form a third angle with the central axis and/or the primary axis. The third angle may be less than 15°. The second angle may be in the range from 75° to 105°, such as 90°±5° or 90°.

In one or more exemplary drug delivery devices, the third attachment part extends, e.g. at least in an activated state of the drug delivery device and optionally in an initial state of the drug delivery device, in a direction optionally away from the drug delivery device. In other words, the third attachment part may extend, e.g. at least in an activated state of the drug delivery device and optionally in an initial state, from an outer surface of the drug delivery device. Formulated differently, the third attachment axis may, e.g. at least in an activated state of the drug delivery device and optionally in an initial state of the drug delivery device form an angle of at least 45° with the central axis and/or the primary axis.

The third attachment part may in a first state of the drug delivery device extend in a third primary direction and in a third state of the drug delivery device extend in a third secondary direction. The third primary direction and the third secondary direction may form an angle of at least 30°. The third primary direction may be parallel or substantially parallel to the central axis. The third primary direction may form an angle less than 60° with the central axis. The third secondary direction may form an angle of at least 60°, such as about 90° with the central axis. The third secondary direction may be perpendicular to the central axis.

The third distal end of the third attachment part may be configured to move or be moved from a third primary position in a first state of the drug delivery device to a third secondary position in the second state.

In one or more exemplary drug delivery devices, further (e.g., multiple) attachment parts may be utilized. They may be rotatably attached to the first body part and/or the second body part and/or the insert. The multiple further attachment parts may include the same components as discussed above with respect to the first attachment part, and/or the second attachment part, and/or the third attachment part.

In one or more exemplary drug delivery devices, the drug delivery device can have a fourth, fifth, and/or sixth attachment element having any or all of the features discussed above.

In one or more exemplary drug delivery devices, the second body part may define a second recess (e.g., cavity, gap, slot, hole, aperture, retainer, second body recess) extending to an outer surface of the second body part. The recess may be formed by solid walls on all sides except an outermost surface, which is open. For example, the second recess may be formed by a first wall, a second wall, and a bottom. The first wall may be opposite the second wall.

The bottom may connect the first wall and the second wall. In one or more exemplary drug delivery devices, the first wall and/or the bottom wall and/or the second wall are flat. In one or more exemplary drug delivery devices, the first wall and/or the bottom wall and/or the second wall are curved. The open outermost surface may be curved to follow along with an outer surface of the carrier.

The second recess may extend along a portion of the outer surface of the second body. The second recess may extend fully along an outer circumference of the second body. The second recess may extend around 10, 15, 20, 25, 30, 35, 40, 45, 50, 55, 60, 65, 70, 75, 80, 85, 90, 95, or 100% of an outer circumference of the second body. The second recess may extend around greater than 10, 15, 20, 25, 30, 35, 40, 45, 50, 55, 60, 65, 70, 75, 80, 85, 90, or 95% of an outer circumference of the second body. The second recess may extend around less than 10, 15, 20, 25, 30, 35, 40, 45, 50, 55, 60, 65, 70, 75, 80, 85, 90, 95, or 100% of an outer circumference of the second body. The second body may optionally contain more than one second recess, for example if an insert and a third attachment part are used. If more than one second recess is used, they may be spaced longitudinally apart and/or circumferentially apart.

The second recess may extend from an outer surface toward the central axis through 5, 10, 15, 20, 25, 30, 35, or 40% of the drug delivery device. The second recess may extend from an outer surface toward the central axis through greater than 5, 10, 15, 20, 25, 30, 35, or 40% of the drug delivery device. The second recess may extend from an outer surface toward the central axis through less than 5, 10, 15, 20, 25, 30, 35, or 40% of the drug delivery device.

In one or more exemplary drug delivery devices, the second recess may extend circumferentially, or partially circumferentially around the second body with the central axis being the longitudinal direction. The second recess may extend perpendicularly with respect to the central axis and/or the primary access (e.g., may extend along a cross section of the drug delivery device perpendicular to the central axis and/or the primary access).

The second recess may have any number of shapes when viewed in cross section with respect to the central axis and/or the primary access. For example, the second recess can be a portion of a circle, such as a half circle. The second recess can be a triangle. The second recess can be a sector of a circle. The second recess can be generally circular in shape, with a portion of the circle cut off. For example, the portion of the circle can be cut off from two points on the circumference of the circle connected by a single straight line. The second recess can be a curved edge connected by two straight edge. The second recess can be two curved edges connected to each other by two straight edges.

For example, in one or more exemplary drug delivery systems, the second recess can form a slice of the second body part. Thus, the second recess can extend greater circumferentially than longitudinally.

In alternate drug delivery devices, the second recess is a cylinder. In alternate drug delivery devices, the second recess is a rectangular prism.

The second recess may be relatively thin. For example, the second recess may be the longitudinal length of the second spike. The first recess may have a longitudinal length slightly longer than the second spike.

In one or more exemplary drug delivery devices, the second recess can have a longitudinal length of 1.1, 1.2, 1.3, 1.4, 1.5, 1.6, 1.7, 1.8, 1.9, 2.0, or 2.1 mm. In one or more exemplary drug delivery devices, the second recess can have a longitudinal length of greater than 1.1, 1.2, 1.3, 1.4, 1.5, 1.6, 1.7, 1.8, 1.9, 2.0, or 2.1 mm. In one or more exemplary drug delivery devices, the second recess can have a longitudinal length of less than 1.1, 1.2, 1.3, 1.4, 1.5, 1.6, 1.7, 1.8, 1.9, 2.0, or 2.1 mm.

In one or more exemplary drug delivery devices, the second recess may have a longitudinal length of 2.6, 2.7, 2.8, 2.9, 3.0, 3.1, 3.2, 3.3, 3.4, 3.5, or 3.5 mm. In one or more exemplary drug delivery devices, the second recess may have a longitudinal length of greater than 2.6, 2.7, 2.8, 2.9, 3.0, 3.1, 3.2, 3.3, 3.4, 3.5, or 3.5 mm. In one or more exemplary drug delivery devices, the second recess may have a longitudinal length of less than 2.6, 2.7, 2.8, 2.9, 3.0, 3.1, 3.2, 3.3, 3.4, 3.5, or 3.5 mm.

In one or more exemplary drug delivery devices, the second recess may have a longitudinal length of 2, 3, 4, 5, 6, 7, 8, 9, 10, 11, 12, 13, 14, or 15 mm. In one or more exemplary drug delivery devices, the second recess may have a longitudinal length of greater than 2, 3, 4, 5, 6, 7, 8, 9, 10, 11, 12, 13, 14, or 15 mm. In one or more exemplary drug delivery devices, the second recess may have a longitudinal length of less than 2, 3, 4, 5, 6, 7, 8, 9, 10, 11, 12, 13, 14, or 15 mm.

In one or more exemplary drug delivery devices, the second recess may have a radius of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the second recess may have a radius of less than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the second recess may have a radius of greater than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm.

The second recess may be parallel to the central axis and/or the primary access. The second recess may be orthogonal to the central axis and/or the primary access. The second recess may be at an angle of 5, 10, 15, 20, 25, 30, 35, 40, 45, 50, 55, 60, 65, 70, 75, 80, or 85 degrees with respect to the central axis and/or the primary access. The second recess may be at an angle of greater than 5, 10, 15, 20, 25, 30, 35, 40, 45, 50, 55, 60, 65, 70, 75, 80, or 85 degrees with respect to the central axis and/or the primary access. The second recess may be at an angle of less than 5, 10, 15, 20, 25, 30, 35, 40, 45, 50, 55, 60, 65, 70, 75, 80, or 85 degrees with respect to the central axis and/or the primary access.

As mentioned, in one or more exemplary drug delivery devices, the drug delivery system can be formed from an insert inserted into a carrier. The drug delivery device can include an insert (e.g., a first insert or a second insert). The insert can be inserted into a recess (e.g., the second recess and/or the body first recess). Alternatively, the drug delivery system can include multiple inserts. Each of the multiple inserts (e.g., a first insert and a second insert) can be inserted into one of the first recess or the second recess. In one or more exemplary drug delivery device, the insert can be inserted into the second recess of the second body part.

The insert can include an insert body. The insert can include the second attachment part. The insert can include the insert recess. The insert recess can be in the insert body. Both the second attachment part and the insert recess are discussed in detail above.

The insert can be sized and configured to be inserted into the second recess. The insert can be configured to releasable fit within the second recess. The insert can be configured to permanently fit within the second recess. The insert body is configured to be fixably arranged within a recess of the drug delivery system. The insert can be configured to be inserted into the second recess via an opening of the outer surface of the second body.

In one or more exemplary drug delivery devices, the insert can conform to the second recess. For example, once attached, the insert body may not move within the second recess. Thus, when inserted, the insert can form an outer surface of the second body part. In one or more exemplary drug delivery devices, insertion of the insert into the second body part may form a fluid tight seal on an outer surface of the delivery system. For example, fluid may not be able to enter the second recess.

The insert body may include an insert mating element (e.g., mating feature, mating protrusions, protrusions). In one or more exemplary drug delivery systems, the second body part can define a body mating element that extends into the second recess. The body mating element may mechanically mate with an insert, such as to the insert mating element. This mating can retain the insert within the second recess. The body mating element may releasably mate with an insert. The body mating element can extend from one and/or both sidewalls of the second body part defining the second recess. The body mating element can extend from the base surface of the second body part defining the second recess. The body mating element can extend along the outer surface of the second body part, such as over a portion of the second recess. The body mating element can be rigid. Alternatively, the body mating element can be flexible.

In one or more exemplary drug delivery devices, the insert mating element and/or the body mating element may form a mechanical fit. For example, when the insert is pressed into the second recess, the insert mating element and/or the body mating element may deform in order to connect the components. In one or more exemplary drug delivery devices, the insert body can be configured to be snap fit to the second body part within the second recess.

Advantageously, the insert can be fixedly inserted into the drug delivery device (e.g., the carrier) via a recess. In one or more exemplary drug delivery systems, the insert can be removed from the drug delivery device. For example, if a sufficient force were applied to the insert away from the carrier, the insert could be released from the carrier. Alternatively, the inert can be electronically released from the carrier. Alternatively, the insert may include a mechanical actuator (e.g., button, snap, component) that releases the insert from the carrier.

In one or more exemplary drug delivery devices, the insert can be refilled with an active drug substance and the insert can be reinserted into the carrier for additional use.

In one or more exemplary drug delivery devices, the first body part can include a first recess and the second body part can include a second recess.

The first recess and/or the second recess can be sized and configured for an insert to be fixedly inserted into the first recess and/or the second recess.

In one or more exemplary drug delivery systems using a first insert and a second insert, the first recess may be sized and configured for the first insert to be fixedly inserted into the first recess and the second recess may be sized and configured for the second insert to be fixedly inserted into the second recess. In one or more exemplary drug delivery systems, the first insert and the second insert can have the same shape. Thus, the first insert can be fixedly inserted into the second recess and the second insert can be fixedly inserted into the first recess. In one or more exemplary drug delivery systems, the first insert and the second insert can have different dimensions. Thus, the first insert may only be configured to be fixedly inserted into the first recess and the second insert may only be configured to be fixedly inserted into the second recess.

In one or more exemplary drug delivery systems, the drug delivery system can further include a cover element (e.g., cover, shield, protector, lock, cover band, first cover band, first cover element). The cover element can be used in conjunction with a locking mechanism being used on the drug delivery device. The cover element can be used without a locking mechanism being used on the drug delivery device.

The cover element may form of a cover element body (e.g., partial cylinder, band, ring, loop, partial ring, partial loop). The cover element body may have a circumferential length greater than a longitudinal width. For example, the circumferential length may be 2×, 3×, 4×, 5×, 6×, 7×, 8×, 9×, or 10× the longitudinal width.

The cover element may have a longitudinal length of 6.0, 6.1, 6.2, 6.3, 6.4, 6.5, 6.6, 6.7, 6.8, 6.9, or 7.0 mm. The cover element may have a longitudinal length of greater than 6.0, 6.1, 6.2, 6.3, 6.4, 6.5, 6.6, 6.7, 6.8, 6.9, or 7.0 mm. The cover element may have a longitudinal length of less than 6.0, 6.1, 6.2, 6.3, 6.4, 6.5, 6.6, 6.7, 6.8, 6.9, or 7.0 mm.

In one or more exemplary drug delivery devices, the cover element may have a longitudinal length of 2.6, 2.7, 2.8, 2.9, 3.0, 3.1, 3.2, 3.3, 3.4, 3.5, or 3.5 mm. In one or more exemplary drug delivery devices, the cover element may have a longitudinal length of greater than 2.6, 2.7, 2.8, 2.9, 3.0, 3.1, 3.2, 3.3, 3.4, 3.5, or 3.5 mm. In one or more exemplary drug delivery devices, the cover element may have a longitudinal length of less than 2.6, 2.7, 2.8, 2.9, 3.0, 3.1, 3.2, 3.3, 3.4, 3.5, or 3.5 mm.

In one or more exemplary drug delivery devices, the cover element may have a longitudinal length of 2, 3, 4, 5, 6, 7, 8, 9, 10, 11, 12, 13, 14, or 15 mm. In one or more exemplary drug delivery devices, the cover element may have a longitudinal length of greater than 2, 3, 4, 5, 6, 7, 8, 9, 10, 11, 12, 13, 14, or 15 mm. In one or more exemplary drug delivery devices, the cover element may have a longitudinal length of less than 2, 3, 4, 5, 6, 7, 8, 9, 10, 11, 12, 13, 14, or 15 mm.

The cover element may have a radius of 5.5, 5.6, 5.7, 5.8, 5.9, 6.0, 6.1, 6.2, 6.3, 6.4, or 6.5 mm. The cover element may have a radius of less than 5.5, 5.6, 5.7, 5.8, 5.9, 6.0, 6.1, 6.2, 6.3, 6.4, or 6.5 mm. The cover element may have a radius of greater than 5.5, 5.6, 5.7, 5.8, 5.9, 6.0, 6.1, 6.2, 6.3, 6.4, or 6.5 mm.

In one or more exemplary drug delivery devices, the cover element may have a radius of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the cover element may have a radius of less than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In one or more exemplary drug delivery devices, the cover element may have a radius of greater than 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm.

The cover element body may have a longitudinal length of 3.0, 3.1, 3.2, 3.3, 3.4, 3.5, 3.6, 3.7, 3.8, 3.9, or 4.0 mm. The cover element body may have a longitudinal length of less than 3.0, 3.1, 3.2, 3.3, 3.4, 3.5, 3.6, 3.7, 3.8, 3.9, or 4.0 mm. The cover element body may have a longitudinal length of greater than 3.0, 3.1, 3.2, 3.3, 3.4, 3.5, 3.6, 3.7, 3.8, 3.9, or 4.0 mm.

In one or more exemplary drug delivery devices, the cover element may fit on an outer surface of the drug delivery device and/or the carrier. The cover element may fit on an outer surface of the first body. The cover element may fit on an outer surface of the second body. For example, the cover element may be snap fit onto an outer surface of the drug delivery device. The cover element may include a cover attachment element configured to fit within a mating recess of the drug delivery device.

In one or more exemplary drug delivery devices, the cover element could be in the shape of a capsule part. For example, the cover element could form a first half of a capsule. A first cover element could form a first half of a capsule and a second cover element could form a second half of the capsule. When fitted together, the first cover element and the second cover element could form a full capsule.

In one or more exemplary drug delivery devices, the cover element may fit on an outer surface of the insert. The cover element may releasably attach to the insert. The cover element may be mechanically fit onto the insert. For example, the cover element may be snap fit onto the insert. The cover element may be chemically attached onto the insert. In one or more exemplary drug delivery device, the cover element can be attached to the insert prior to the insert being inserted into the carrier. In alternative embodiments, the cover element can be attached to the insert after the insert is inserted into the carrier.

The cover element may partially or fully cover the insert recess. Thus, the cover element may prevent motion of the second attachment part. The cover element may partially or fully cover both the first body recess and the insert recess. A first cover element may partially or fully cover the first body recess and a second cover element may partially or fully cover the insert recess.

The cover element may extend fully along an outer circumference of the drug delivery device. The cover element may extend around 10, 15, 20, 25, 30, 35, 40, 45, 50, 55, 60, 65, 70, 75, 80, 85, 90, 95, or 100% of an outer circumference of the drug delivery device. The cover element may extend around greater than 10, 15, 20, 25, 30, 35, 40, 45, 50, 55, 60, 65, 70, 75, 80, 85, 90, or 95% of an outer circumference of the drug delivery device. The cover element may extend around less than 10, 15, 20, 25, 30, 35, 40, 45, 50, 55, 60, 65, 70, 75, 80, 85, 90, 95, or 100% of an outer circumference of the drug delivery device.

In one or more exemplary drug delivery devices, the cover element may include one or more mating protrusions (e.g., extensions, tabs, fingers, projections, teeth). For example, the cover element may include 1, 2, 3, 4, 5, 6, 7, 8, 9, or 10 mating protrusions. The mating protrusions may only extend longitudinally from one side of the cover element. The mating protrusions may extend longitudinally from both sides of the cover element. The mating protrusions may be equally spaced along the cover element. The mating protrusions may be unequally spaced along the cover element.

The one or more mating protrusions may extend towards a longitudinal center of the drug delivery device (e.g., along an outer surface of the body towards the second body part if the cover element is located on an insert in the first body part, or along an outer surface of the body towards the first body part if the cover element is located on an insert in the second body part).

In one or more exemplary drug delivery devices, the drug delivery device may include mating features. The mating features can be configured to mate, e.g. receive, hold, contact, with the one or more mating protrusions of the cover element. The mating features can include one or more body mating protrusions (e.g., extensions, tabs, fingers, projections, teeth) extending radially outward from an outer surface of the drug delivery device. The mating features can extend from the first body part, the second body part, or both. The mating features can be formed in one or more circumferential rows. For example, there can be one circumferential row of mating features or two circumferential rows of mating features. Both circumferential rows can be on the same body part (e.g., the first body part or the second body part). In alternative implementations, one circumferential row of mating features can be on the first body part and a second circumferential row of mating features can be on the second body part.

The one or more mating protrusions may be triangular, square, rectangular, rounded, or other polygonal shapes. The one or more mating protrusions may vary in shape along the cover element. The one or more mating protrusions may be angled in a circumferential direction to form a mating recess (e.g., curve, cavity, space, gap). This mating recess can help fit the one or more body mating protrusions to the one or more protrusions of the cover element. Further, the mating recess can prevent unwanted release of the cover element.

Accordingly, when the first cover band is attached to the drug delivery device, the one or more mating protrusions can fit between the one or more mating features. The one or more mating protrusions can fit within adjacent mating features. This can help properly align the cover element.

In some implementations the mating features may be recesses extending internally into the drug delivery device. The mating protrusions can then extend radially inward instead of longitudinally to mate with the mating features. In one or more exemplary drug delivery devices, rotation of the first body part with respect to the second body part can cause the cover element to translate, e.g. move, change position, relocate. For example, rotation can cause the cover element to translate along the central axis. This translation can expose the first attachment part and/or the second attachment part, depending on the coverage of the cover element. This can occur, for example, as the mating protrusions can squeeze triangle-shaped mating protrusions, or other shaped mating protrusions, pushing them longitudinally away. The translation can fully translate the cover element off of the drug delivery device.

The translation can partially translate the cover element to expose the first attachment part and/or the second attachment part with the cover band associated with, e.g. attached to, the drug delivery device.

In one or more exemplary drug delivery devices, the drug delivery device and/or carrier can contain a longitudinal slot and/or a pair of longitudinal slots on an outer surface. The cover element can be configured to be partially held within the longitudinal slot, and can translate along the longitudinal slot to expose the first attachment part and/or the second attachment part. Alternatively, the drug delivery device may not contain a longitudinal slot, and the cover element can translate along an outer surface of the carrier/delivery device.

As mentioned, the cover element can be used with a locking mechanism. When used as a locking mechanism, the cover element can include any and all of the features discussed above with respect to the cover element. In one or more exemplary drug delivery devices, the cover element can be the locking mechanism. For example, the cover element can be used to lock the first body part with relation to the second body part (and thus the insert). The cover element can be used to lock the insert to the first body part. The cover element can be used to lock the insert to the second body part.

In one or more exemplary drug delivery devices, the cover element may include one or more locking protrusions (e.g., cover element protrusions, extensions, tabs, fingers, projections, teeth). For example, the cover element may include 1, 2, 3, 4, 5, 6, 7, 8, 9, or 10 locking protrusions. The cover element may only extend longitudinally from one side of the cover element. The locking protrusions may extend longitudinally from both sides of the cover element. The locking protrusions may be equally spaced along the cover element. The locking protrusions may be unequally spaced along the cover element. In one or more exemplary drug delivery devices, the cover element may include at least one protrusion configured to mate with a slot on the first body part and/or the second body part. The one or more locking protrusions may extend towards a longitudinal center of the drug delivery device (e.g., along an outer surface of the body towards the second body part if the first locking band is located on the first body part, or along an outer surface of the body towards the first body part if the first locking band is located on the second body part/insert).

The one or more locking protrusions may be triangular, square, rectangular, rounded, or other polygonal shapes. The one or more locking protrusions may vary in shape along the cover element.

In one or more exemplary drug delivery devices, the drug delivery device may include mating features. The mating features can be configured to mate with the one or more protrusions of the cover element. The mating features can include one or more mating protrusions (e.g., extensions, tabs, fingers, projections, teeth) extending radially outward from an outer surface of the drug delivery device. The mating features can extend from the first body part, the second body part, or both. The mating features can be formed in one or more circumferential rows. For example, there can be one circumferential row of mating features or two circumferential rows of mating features. Both circumferential rows can be on the same body part (e.g., the first body part or the second body part). In alternative implementations, one circumferential row of mating features can be on the first body part and a second circumferential row of mating features can be on the second body part.

The one or more mating protrusions may be triangular, square, rectangular, rounded, or other polygonal shapes. The one or more mating protrusions may vary in shape along the first locking band. The one or more mating protrusions may be angled in a circumferential direction to form a mating recess (e.g., curve, cavity, space, gap). This mating recess can help lock the one or more mating protrusions to the one or more protrusions of the first locking band. Further, the mating recess can prevent unwanted release of the cover element.

Accordingly, when the cover element is attached to the drug delivery device, the one or more locking protrusions can fit between the one or more mating protrusions. The one or more locking protrusions can fit within adjacent mating protrusions. This can prevent rotation of the first body with respect to the second body and insert. For example, the first body will be impeded in rotating by the cover element. In some embodiments, the locking protrusion can be located between two mating protrusions, each of the mating protrusions angled in opposite directions to hold the locking protrusion in place.

In some implementations the mating features may be recesses extending internally into the drug delivery device. The locking protrusions can then extend radially inward instead of longitudinally to mate with the mating features.

As discussed above, when the cover element is attached and the one or more protrusions mate with the mating features, the first body part is locked in place with relation to the second body part. Specifically, the cover element may be configured to rotationally lock the first body part in relation to the second body part, or vice versa. The first body part and the second body part may be released from the cover element when the cover element dissolves as discussed herein.

Further, the dissolving of the cover element can allow the second attachment part to further rotate out of the insert recess. Thus, when the first body and the second body rotate with respect to one another, the first attachment part and the second attachment part can rotate for inserting into tissue. If the cover element is not used to lock the first body part to the second body part, dissolving of the cover element can allow the second attachment part to extend outside of the insert.

In one or more exemplary drug delivery devices, the cover element can at least partially cover the second attachment part. The cover element may also cover the insert recess of the insert. In one or more exemplary drug delivery devices, the cover element is configured to prevent motion of the second attachment part. In alternative embodiments, the cover element may not be configured to prevent motion of the second attachment part.

In one or more exemplary drug delivery devices, the cover element can include a plurality of square-shaped locking protrusions and a plurality of triangle-shaped locking protrusions. The square-shaped locking protrusions may be used to keep the cover element in place under the force of the mating protrusions. The triangle-shaped locking protrusions may be used to properly locate the cover element.

In one or more exemplary drug delivery systems, the whole of the cover element can be dissolvable. In one or more exemplary drug delivery systems, only the square-shaped locking protrusions may be formed from a dissolvable material. Once the square-shaped locking protrusions dissolve, the first body part and the second body part may be allowed to rotate. Rotation of the first body part with respect to the second body part can cause the cover element to translate, e.g. move, change position, relocate. This can occur as the mating protrusions can squeeze the triangle-shaped locking protrusions, pushing them longitudinally away. For example, rotation can cause the cover element to translate along the central axis.

This translation can expose the first attachment part and/or the second attachment part, depending on the coverage of the cover element. The translation can fully translate the cover element off of the drug delivery device. The translation can partially translate the cover element to expose the first attachment part and/or the second attachment part with the cover element remaining associated with, e.g. attached to, the drug delivery device.

As mentioned, the drug delivery device comprises an actuator mechanism. The actuator mechanism is configured to move the first attachment part in relation to the second attachment part, such as configured to move the first distal end towards and/or away from the second distal end, e.g., at least during a part of a rotation, such as in a first rotation and optionally in a second rotation. In one or more exemplary delivery devices, the actuator mechanism is configured to move the first distal end towards the second distal end. To move the first distal end towards the second distal end may be understood as reducing a distance between the first distal end and the second distal end. To move the first distal end towards the second distal end may be understood as reducing an angle between the first attachment axis and the second attachment axis, such as reducing an angle between a first secondary direction of the first attachment part and a second secondary direction of the second attachment part. In one or more exemplary drug delivery devices, the actuator mechanism reduces the distance between the first distal end and the second distal end during rotation of the first body part with respect to the second body part around the central axis.

In one or more exemplary drug delivery devices, the actuator mechanism is configured to move the first distal end towards the second distal end by rotating, e.g., in a second state of the drug delivery device, the first body part in relation to the second body part and/or vice versa. The actuator mechanism may be configured to rotate the first body part at least 90°, such as at least 450°, at least 810°, at least 1170°, at least 1530°, or even at least 1890° in relation to the second body part about the primary axis. The actuator mechanism may be configured to rotate the first body part in relation to the second body part about the primary axis in a stepwise manner. In other words, to rotate the first body part in relation to the second body part about the primary axis may comprise a plurality of rotations including a first rotation and a second rotation, e.g. a first rotation followed by a first time period with reduced or no rotation followed by a second rotation. A first rotation followed by a second rotation after a first time period may increase the possibility of the drug delivery device attaching to the biological tissue. The first time period or in general time periods between rotations allows the drug delivery to move to other positions in the gastrointestinal tract. In other words, if the drug delivery does not attach to the biological tissue during a first rotation, further rotations increases the chance of attachment to the internal tissue. The first rotation may be at least 90°, and the second rotation may be at least 180°. The plurality of rotations may comprise a third rotation. The third rotation may be at least 180°.

In one or more exemplary drug delivery devices, a movement of the first distal end towards the second distal end may be preceded by and/or followed by a movement of the first distal end away from the second distal end. In other words, a movement of the first distal end towards the second distal end may be prior to and/or after movement of the first distal end away from the second distal end. For example, a first rotation may comprise moving the first distal end towards the second distal end and/or moving the first distal end away from the second distal end. For example, a second rotation may comprise moving the first distal end towards the second distal end and/or moving the first distal end away from the second distal end. For example, a third rotation may comprise moving the first distal end towards the second distal end and/or moving the first distal end away from the second distal end.

The actuator mechanism optionally comprises a resilient part such as a spring element configured to apply force to the first body part and/or the second body part. The resilient part may comprise a first part, such as a first end, connected to the first body part. The resilient part may comprise a second part, such as a second end, connected to the second body part and/or the insert.

In one or more exemplary drug delivery devices, the actuator mechanism optionally comprises a swelling media, i.e., a media increasing its volume, e.g., upon contact with a fluid, e.g., in order to provide rotation of parts in relation to each other. In one or more exemplary drug delivery devices, a swelling medial provides rotation of the first attachment part in relation to the first body part and/or provides rotation of the second attachment part in relation to the second body part. In one or more exemplary drug delivery devices, a swelling medial provides rotation of the first body part in relation to the second body part.

The actuator mechanism, such as the resilient part, may be configured to rotate the first attachment part about the first rotation axis in relation to the first body part.

The actuator mechanism, such as the resilient part, may be configured to rotate the second attachment part about the second rotation axis in relation to the second body part.

In one or more exemplary drug delivery devices, drug delivery device comprises a chamber, the drug delivery device being configured to deliver an active drug substance from the chamber to the surroundings of the drug delivery device. In one or more exemplary drug delivery devices, the first attachment part and/or the second attachment part comprises a chamber), the drug delivery device being configured to deliver an active drug substance from the chamber to the surroundings of the drug delivery device.

In one or more exemplary drug delivery devices, the first body part can receive a first insert and the second body part can receive a second insert. In one or more exemplary drug delivery devices, the first insert comprises a first attachment part having a first chamber, the drug delivery device being configured to deliver an active drug substance from the first chamber to the surroundings of the drug delivery device. In some implementations, the second insert may have a second attachment part which does not contain a chamber. In alternative implementations, the second insert has a second attachment part having a second chamber, the drug delivery device being configured to deliver an active drug substance from the first chamber and the second chamber to the surroundings of the drug delivery device.

The chamber may be arranged in the second attachment part, such as in the second spike, e.g., within a distance of 8 mm, such as within 5 mm, from the first distal end. The second attachment part, such as the second spike may have one or more openings providing access to the chamber. In one or more exemplary drug delivery devices, the chamber is formed as a through-going bore in the first spike.

The chamber may be a compartment which is inside the second attachment part, where the penetration of the second attachment part into a biological tissue may release a drug substance in the first compartment into the biological tissue. Additionally or alternatively, the chamber may be compartment that is in the form of a depression or opening or spike or hollow spike on the outer surface of the first and/or the second body part, where the drug delivery device may be adapted to release the drug substance inside the organ of the body which the drug delivery device is adapted to pass through.

In one or more exemplary drug delivery devices, the first compartment may be open from an inner volume of the drug delivery device and towards an outer part of the drug delivery device. In one or more examples, the first compartment may be inside the removable insert, and where the first compartment is in fluid connection with the second attachment part, so that when the second distal end of the second attachment part has penetrated the biological tissue, the drug substance may be released from the first compartment and into the biological tissue via the second attachment part. This may e.g., be where the second attachment part is a tubular part, which has a second distal end in fluid communication with the first compartment of the drug delivery device.

In one or more exemplary drug delivery devices, the drug delivery device comprises a second compartment, the drug delivery device being configured to deliver an active drug substance from the second compartment to the surroundings of the drug delivery device. The second compartment may be arranged in the first attachment part or in the second attachment part, such as in the second spike, e.g., within a distance of 8 mm, such as within 5 mm, from the second distal end. The second attachment part, such as the second spike may have one or more openings providing access to the second compartment. In one or more exemplary drug delivery devices, the second compartment is formed as a through-going bore in the first spike or in the second spike.

In one or more exemplary drug delivery devices, the first attachment part and the second attachment part form an angle when the first distal end and the second distal end are in a plane that includes the primary axis when the insert is loaded into the drug delivery device. In other words, the first attachment axis and the second attachment may form an angle, e.g., larger than 5°, such as in the range from 10° to 75°, when the first distal end and the second distal end are in a plane that includes the primary axis. In one or more exemplary drug delivery devices, the first attachment part and the second attachment part comprise a first spike and a second spike, respectively.

In one or more exemplary drug delivery devices, the drug delivery device has a first state, also denoted initial state, where the first body part and the second body part are rotationally stationary relative to each other and a second state, also denoted activated state, where the first body part and the second body part and insert are rotationally mobile relative to each other, e.g., can rotate about the primary axis of the drug delivery device. In other words, the first body part may be locked, e.g., prevented from rotating, in relation to the second body part and insert. The first state may e.g., be an initial state or introduction state, where the drug delivery device is adapted to be introduced into the body, and where the first body part and the second body part are stationary relative to each other, and where the insert is loaded into the second body part. In the first state the resilient part may have a predefined amount of stored energy, where the energy level is stationary in the resilient part while the body parts are stationary.

In one or more exemplary drug delivery devices, the drug delivery device has a first state where the resilient part has a constant resilient force load and a second state where the resilient part at least partly releases the resilient force load. In other words, the resilient part may be biased or preloaded in the first state of the drug delivery and upon release, e.g., by release of a locking mechanism, (i.e., the drug delivery device being in the second state) the force from the resilient part may affect a rotation of the first body part in relation to the second body part, i.e., including a movement of the first distal end towards the second distal.

In one or more exemplary drug delivery devices, the actuator mechanism is configured to move the first distal end from a first primary position, e.g. in first state of the drug delivery device, with a first primary radial distance from a central axis of the delivery device to a first secondary position, e.g. in second state of the drug delivery device, with a first secondary radial distance from the central axis and/or primary axis, wherein the first secondary radial distance is larger than the first primary radial distance. Thus, the first distal end of the first attachment may be in a first primary position when the drug delivery device is in the first state and/or the first distal end of the first attachment part may be in a first secondary position when the drug delivery device is in the second state.

The first primary radial distance may be less than 10 mm, such as less than 8 mm or even less than 5 mm. The first secondary radial distance may be larger than the first primary radial distance. The first secondary radial distance may be larger than 5 mm, such as larger than 6 mm, or larger than 8 mm. In one or more exemplary drug delivery devices, the first secondary radial distance is in the range from 6 mm to 15 mm.

In one or more exemplary drug delivery devices, the first attachment part, such as a part of the first spike and/or the first distal end, may, in the first state be arranged or at least partly arranged within a first primary recess of the first body part. In the first state, the first distal end may be arranged inside the first body part.

In one or more exemplary drug delivery devices, the first attachment part, such as a part of the first spike and/or the first distal end, may, in the second state be arranged or at least partly arranged outside the first primary recess of the first body part.

In one or more exemplary drug delivery devices, the first attachment part, such as a part of the first spike and/or the first distal end, may, in the first state be arranged within a second primary recess of the second body part. Thereby, the first attachment part may be configured to lock the first body part in relation to the second body part in the first state of the drug delivery device.

In one or more exemplary drug delivery devices, the first attachment part, such as a part of the first spike and/or the first distal end, may, in the second state be arranged outside the second body part and/or at least outside the second primary recess of the second body part.

In one or more exemplary drug delivery devices, the actuator mechanism is configured to move the second distal end from a second primary position, e.g. in first state of the drug delivery device, with a second primary radial distance from a central axis of the delivery device to a second secondary position, e.g. in second state of the drug delivery device, with a second secondary radial distance from the central axis and/or primary axis, wherein the second secondary radial distance is larger than the second primary radial distance. Thus, the second distal end of the second attachment may be in a second primary position when the drug delivery device is in the first state and/or the second distal end of the second attachment part may be in a second secondary position when the drug delivery device is in the second state.

The second primary radial distance may be less than 10 mm, such as less than 8 mm or even less than 5 mm. The second secondary radial distance may be larger than the second primary radial distance. The second secondary radial distance may be larger than 5 mm, such as larger than 6 mm, or larger than 8 mm. In one or more exemplary drug delivery devices, the second secondary radial distance is in the range from 6 mm to 15 mm.

In one or more exemplary drug delivery devices, the second attachment part, such as a part of the second spike and/or the second distal end, may, in the first state be arranged or at least partly arranged within a first secondary recess of the first body part. Thereby, the second attachment part may be configured to lock the first body part in relation to the second body part in the first state of the drug delivery device. In the first state, the second distal end may be arranged inside the second body part.

In one or more exemplary drug delivery devices, the second attachment part, such as a part of the second spike and/or the second distal end, may, in the second state be arranged or at least partly arranged outside the first body part and/or at least outside the first secondary recess of the first body part.

In one or more exemplary drug delivery devices, the second attachment part, such as a part of the second spike and/or the second distal end, may, in the first state be arranged within a second secondary recess of the second body part.

In one or more exemplary drug delivery devices, the second attachment part, such as a part of the second spike and/or the second distal end, may, in the second state be arranged outside the second secondary recess of the insert.

In one or more exemplary drug delivery devices, the actuator mechanism is configured to move, e.g., by rotation about a first rotation axis of the first attachment part (first base part), the first distal end from a first primary angular position of first primary position to a first secondary angular position of first secondary position in relation to a first proximal end of the first attachment part. An angle between the first primary angular position and the first secondary angular position may be larger than 10°, such as larger than 45° or larger than 60°.

In one or more exemplary drug delivery devices, the actuator mechanism is configured to move, e.g., by rotation about a second rotation axis of the second attachment part (second base part), the second distal end from a second primary angular position of second primary position to a second secondary angular position of second secondary position in relation to a second proximal end of the second attachment part. An angle between the second primary angular position and the second secondary angular position may be larger than 10°, such as larger than 45° or larger than 60°.

In one or more exemplary drug delivery devices, the drug delivery device comprises a locking mechanism. The locking mechanism may be the cover element as discussed above.

Alternatively, the locking mechanism be different from the cover element. Thus, both a cover element and a locking mechanism can be used. In one or more exemplary embodiments, the cover element can act as the locking element discussed above and the locking mechanism can be used as well. In one or more exemplary embodiments, the cover element does not act as a locking element and the locking mechanism can be the only locking element.

The locking mechanism may be configured to lock, e.g., prevent rotation of the first body part in relation to the second body part and insert in a first state of the drug delivery device. The locking mechanism may be configured to lock the first attachment part in a first primary position, e.g., in relation to the first body part, when the drug delivery device is in the first state. Upon release of the locking mechanism, the first attachment part may be allowed to move from a first primary position to a first secondary position. The locking mechanism may upon release be configured to allow rotation of the first body part in relation to the second body part and insert, e.g., in a second state of the drug delivery device. The locking mechanism may be configured to lock the second attachment part in a second primary position, e.g., in relation to the removable insert, when the drug delivery device is in the first state. The locking mechanism may upon release be configured to allow the second attachment part to move from a second primary position to a second secondary position.

The locking mechanism may comprise a first locking element optionally configured to lock and/or unlock (release) the first body part in relation to the second body part and insert. The first locking element may be configured to lock and/or unlock (release) the first attachment part in relation to the first body part. The first locking element may be configured to lock and/or unlock (release) the second attachment part in relation to the insert. The first locking element may be arranged in a first primary recess of the first body part and/or in a second primary recess of the insert. The first locking element may be configured to dissolve when the drug delivery device enters the gastrointestinal tract or at a desired location in the gastrointestinal tract, thereby releasing the first body part in relation to the second body part and the insert and allowing the actuator mechanism to rotate the first body part in relation to the second body part and insert and thereby moving the first distal end towards the second distal end in turn resulting in attachment of the drug delivery device to the internal tissue.

The locking mechanism may comprise a second locking element optionally configured to lock and/or unlock (release) the first body part in relation to the second body part, and thus the insert. The second locking element may be configured to lock and/or unlock (release) the second attachment part in relation to the insert. The second locking element may be arranged in a first secondary recess of the first body part and/or in a second secondary recess of the insert. The second locking element may be configured to dissolve when the drug delivery device enters the gastrointestinal tract, thereby unlocking or releasing the first body part in relation to the second body part and allowing the actuator mechanism to rotate the first body part in relation to the second body part and the insert and thereby moving the first distal end towards the second distal end in turn resulting in attachment of the drug delivery device to the internal tissue.

The material and/or properties of the cover element and/or the first locking element and/or the second locking element may be selected such that the release of the body parts and/or activation of the drug delivery is controlled to take place at a desired location in the gastrointestinal tract, such as in the stomach or in the intestines. The material of the cover element and/or the first locking element and/or the second locking element may comprise one or more of sugars, sugar derivatives, hydrophilic polymers, pH dependent polymers, and pharmaceutically acceptable excipients that disperses, dissolves, swells, and/or gels upon contact with water/fluid.

In one or more exemplary drug delivery devices, at least part of the first attachment part and/or the second attachment part may be made of a biodegradable material, absorbable material, or similar material which allows the material of the attachment part to be broken down, degraded and/or dissolved by processes that are present in the body, such as corrosion, degradation, hydrolysis and/or proteolytic enzymatic degradation. Thus, when the attachment part(s) has been inside the human body for a period of time, the attachment part(s) may dissolve, decompose or degrade to such a degree that the attachment part may lose its structural stability, which may in turn release the drug delivery device from the surface it has attached itself to. Thus, after a period, e.g., when the drug substance has been released from the attachment part(s), the attachment part(s) may deteriorate to such a degree that the drug delivery device may be released and may continue its journey through the gastrointestinal tract to be released through natural intestinal and/or bowel movements of the user or patient.

In one or more exemplary drug delivery devices, the rotational axis of the first body part and/or the second body part (primary axis) may be the central axis of the drug delivery device, e.g., the primary axis of the first body part may be coaxial to the central axis. Thus, the central axis intersects both the first body part and the second body part, and may define the primary axis.

In one or more exemplary drug delivery devices, the first body part and the second body part when the insert is inserted may be substantially symmetrical in a radial direction perpendicular to the central axis. This may mean that the first body part and/or the second body part may have a circular periphery, where the periphery may extend in a radial direction away from and perpendicular to the central axis.

The first attachment axis may be seen as an axis that is coaxial with the length of the first attachment part. The second attachment axis may be seen as an axis that is coaxial with the length of the second attachment part. In case the first attachment part has a shape that is not straight, the first attachment axis may be defined as an axis that intersects the first distal end and the first proximal end of the first attachment part. In case the second attachment part has a shape that is not straight, the second attachment axis may be defined as an axis that intersects the second distal end and the second proximal end of the second attachment part.

In one or more exemplary drug delivery devices, the first attachment axis may be positioned at a first distance from the central axis, while the second attachment axis may be positioned at a second distance from the central axis and/or primary axis.

For example, the first attachment axis may be positioned at a first primary distance from the central axis in the first state of the drug delivery device. The first primary distance may be larger than 0.5 mm, such as in the range from 1 mm to 15 mm or larger than 1 mm, e.g., 2 mm, 3 mm, 4 mm, 5 mm, 6 mm, 7 mm, 8 mm, 9 mm, 10 mm, 11 mm, 12 mm, 13 mm, or 14 mm.

The first attachment axis may cross or be close to (distance less than 0.5 mm) the central axis in the first state of the drug delivery device.

The first attachment axis may be positioned at a first secondary distance from the central axis in the second state of the drug delivery device. The first secondary distance may be larger than 0.5 mm, such as in the range from 1 mm to 15 mm or larger than 1 mm, e.g., 2 mm, 3 mm, 4 mm, 5 mm, 6 mm, 7 mm, 8 mm, 9 mm, 10 mm, 11 mm, 12 mm, 13 mm, or 14 mm.

The first attachment axis may cross or be close to (distance less than 0.5 mm) the central axis in the second state of the drug delivery device.

For example, the second attachment axis may be positioned at a second primary distance from the central axis in the first state of the drug delivery device. The second primary distance may be larger than 0.5 mm, such as in the range from 1 mm to 15 mm or larger than 1 mm, e.g., 2 mm, 3 mm, 4 mm, 5 mm, 6 mm, 7 mm, 8 mm, 9 mm, 10 mm, 11 mm, 12 mm, 13 mm, or 14 mm.

The second attachment axis may cross or be close to (distance less than 0.5 mm) the central axis in the first state of the drug delivery device.

The second attachment axis may be positioned at a second secondary distance from the central axis in the second state of the drug delivery device. The second secondary distance may be larger than 0.5 mm, such as in the range from 1 mm to 15 mm or larger than 1 mm, e.g., 2 mm, 3 mm, 4 mm, 5 mm, 6 mm, 7 mm, 8 mm, 9 mm, 10 mm, 11 mm, 12 mm, 13 mm, or 14 mm.

The second attachment axis may cross or be close to (distance less than 0.5 mm) the central axis in the second state of the drug delivery device.

In one or more exemplary drug delivery devices, the first attachment part (first attachment axis) and/or the second attachment part (second attachment axis) may be configured to be at an angle to each other when they intersect a plane that includes the central axis. The plane may be a plane that contains the central axis, where the plane also includes a radial axis extending at a right angle from the central axis. When the first attachment part intersects the plane, the first attachment axis of the first attachment part may be at an angle to the plane so that the first distal end of the first attachment part is the first part of the first attachment part that intersects the plane, where the remaining parts of the first attachment part intersects the plane subsequently during rotational movement. The second attachment part may intersect the same plane from the opposite side, where the second distal end of the second attachment part is the first part of the second attachment part that intersects the plane, where the remaining parts of the second attachment part intersects the plane subsequently during rotational movement. Thus, the second attachment part optionally intersects the plane from an opposing rotational direction than the first attachment part. This may also mean that when the first distal end and the second distal end of respective first attachment part and second attachment parts each contact the plane, the first attachment part (first attachment axis) is at an angle to the plane as well as at an angle to the second attachment part (second attachment axis). The angle between the first attachment part (first attachment axis) and the second attachment part (second attachment axis) to the plane may be approximately half the size of the angle between the first attachment part and the second attachment part.

In one or more exemplary drug delivery devices, the first body part may be configured to rotate in a first direction and the second body part with the insert may be configured rotate in a second direction, where the first direction is opposite to the second direction. Thus, as an example, the first body part may rotate in a clockwise direction, while the second body part may rotate in an opposed anti clockwise direction. In one or more examples where the drug delivery device comprises three or more body parts, abutting or neighbouring body parts may rotate in opposite directions. This may also mean that every second body part may rotate in the same direction. For example, where a first body part and a third body part rotate in the same first direction, then a second body part and/or a fourth body part may rotate in a second direction opposite the first direction.

In one or more exemplary drug delivery devices, the actuator mechanism may comprise one or more resilient parts, such as a plurality of resilient parts.

In one or more exemplary drug delivery devices, the first distal end of the first attachment part and/or the second distal end of the second attachment part may be provided with a sharp tip configured to penetrate a biological tissue. The sharp tip may be positioned in the vicinity of the distal end of the respective attachment part, where the sharp tip may be configured to have a diameter at the distal end which is smaller than a diameter of the attachment part at a distance from the distal end. The sharp tip may be configured in such a manner that when a rotational force is applied to the first attachment part, and a counterforce is applied to the second attachment part, the counterforce may cause the sharp tip to penetrate the biological tissue due to the force applied by the actuator mechanism.

When the first attachment part and/or the second attachment part penetrates the biological tissue due to the rotation between the first body part and the second body part with the insert (the first distal end moving towards the second distal end, the respective penetration point(s) in the biological tissue may be utilized to deliver a drug substance from the drug delivery device into the biological tissue, and where the drug substance may be introduced into the biological tissue that is beyond the mucous membrane. Thereby, the drug substance may enter the bloodstream more easily than if the drug substance is released in the stomach or intestinal lumen, and the drug delivery may be more effective. An example of this is when the drug substance is insulin, where insulin may degrade inside the gastrointestinal tract and is not capable of being absorbed from the gastrointestinal tract, but where a mucous membrane has been penetrated, and the insulin released through the penetrated gastrointestinal wall, the insulin will remain intact and reach the bloodstream of the user via the blood vessels in the intestinal layer beyond the mucous membrane (surface).

In one or more exemplary drug delivery devices, the first attachment part and/or the second attachment part may be provided with a gripping part configured to grip a biological tissue. The gripping part may be utilized to improve traction between the attachment part and a mucous membrane, allowing the attachment part to anchor the drug delivery device inside the body of the user. The gripping part may be a part that increases a mechanical friction between the attachment part and the surface to be attached to, where the gripping part may e.g., have a hook shape, or e.g., a shape where the gripping part of the first attachment part faces the gripping part of the second attachment part, so that the biological tissue which is positioned between the first attachment part and the second attachment part is gripped between the two gripping parts.

In one or more exemplary drug delivery devices, a part of the resilient part may be connected to the first body part and a second part of the resilient part may be connected to the second body part. This means that the resilient part may be utilized to store energy, such as rotational energy or rotational force which is applied to the first body part and the second body part, where the energy is stored in the resilient part. Furthermore, when the energy is released, e.g., when a locking element is dissolved or degraded, the force may be released to both the first body part and the second body part, which in turn transfers the force to the first attachment part and the second attachment part. The resilient part may e.g., be in the form of a helical spiral spring (mainspring) and/or a spiral torsion spring, where the first body part may be wound relative to the second body part by rotating the first body part relative to the second body part. This stores energy in the mainspring by twisting the spiral tighter. The stored force of the mainspring may then rotate the first body part in the opposing direction as the mainspring unwinds. Thus, the force of the mainspring may cause the first attachment part and the second attachment parts to travel in opposing directions, and where the attachment parts may pinch the biological tissue and either pinch the tissue or penetrate the tissue in order to attach the drug delivery device to the biological tissue.

When the drug delivery device has entered the body, and has e.g., entered the desired part in the gastrointestinal tract, the drug delivery device may be configured to transform from the first state to the second state. The transformation may be initiated by different means, where e.g., the first and the second body parts may be held in the first state using a locking mechanism e.g., comprising one or more locking elements made of a dissolvable, expandable or degradable material, where the material reacts with the surroundings, such as fluids, inside the desired body part, thereby unlocking or releasing the locking mechanism. The material of the locking elements may be a material that loses its structural force when in contact with the surroundings inside the desired body part. An example may be where locking element(s) is made of a polymeric material or a sugary substance which may dissolve, expand or degrade when it comes into contact with a certain kind of fluid which may include an enzyme or a certain kind of acid inside the digestive system. When the locking element comes into contact with the reagent, the material may dissolve, expand or degrade over time, and when the rotational force of the drug delivery device exceeds the static force of the locking element, the rotational force may be released via a rotation of the first body part relative to the second body part, or vice versa.

In one or more exemplary drug delivery devices, a locking element may fix an attachment part in a position where the attachment element locks the first body part in relation to the second part, i.e., prevents the first body part from rotating in relation to the second body part. When the locking element dissolves or degrades, the attachment part can move to a secondary position where the attachment part does not lock the first body part in relation to the second part, e.g., by the actuator mechanism causing a rotation of the attachment part about a rotation axis in relation to the body part to which the attachment part is rotationally attached.

The second state of the drug delivery device may be seen as the state which is initiated by the release of energy stored in the actuator mechanism, e.g., resilient part(s) of the actuator mechanism into a rotational force of the first and/or the second body part and/or a rotational force of the first attachment part in relation to the first body part. A termination of the second state may be seen as a point in time where the energy stored in the resilient part becomes stationary again, i.e., when the attachment parts have gripped or penetrated biological tissue and/or the rotational movement between the first body part and the second body part is stopped.

In one or more exemplary drug delivery devices, the drug delivery device may have a first state where the actuator mechanism has a constant resilient force load and a second state where the actuator mechanism releases the resilient force load. In the first state, the constant resilient force load may be seen as the energy stored in the actuator mechanism, and where the resilient force load is larger than zero. The second state may be seen as a state where the actuator mechanism releases its resilient force load, where the resilient force load is reduced, e.g., approaches zero, e.g., by rotating the first body part in relation to the second body part. The second state may be terminated when the attachment parts come into contact with or penetrates a biological tissue and the resilient force load does not change, even though it has not reached zero. Thus, a third state may follow the second state, when the drug delivery device has been attached to a wall of biological material, and the resilient force load is stationary after a resilient force release.

The first attachment part and/or the second attachment part may have an unfolding function, where during the first state of the drug delivery device, i.e., the initial state of the drug delivery device, the attachment parts are positioned or arranged inside the first and/or the insert, or alternatively where the first and/or second attachment parts may be folded along the sides of the body parts. Other ways of obtaining the same may be envisioned. The folded state (first state) may e.g., be maintained using a releasable locking mechanism in the form of an encapsulation similar to a drug substance capsule, a band or plug, e.g., made of gelatine, sugars or other dissolvable materials or materials that lose their structural force.

Thus, the attachment parts may be held in place until the drug delivery device has entered the gastrointestinal tract, e.g., the stomach, so that the attachment parts do not interfere or damage the lining of the mouth and/or the oesophagus. Prior to or during the transition to the second state the attachment parts may extend from the body part/insert and outwards, making the attachment parts ready to interact with a lining of the digestive system. When the attachment part or parts are in a folded or collapsed position, the distance from the central axis to the distal end of the attachment part being longer in the second state than in a first state. Thus, the diameter of the drug delivery device in the first state will be less in than the diameter of the drug delivery device in the second state.

In one or more exemplary drug delivery devices, at least part of the first attachment part and/or the second attachment part, such as the first spike and/or the second spike may be made of material comprising one or more of magnesium, titanium, iron and zinc which allows for accurate and precise control of the size and/or shape/geometry of the first attachment part and/or second attachment part in turn allowing for a delivery device with desired attachment capabilities and/or small production variances which is in particular important in the pharmaceutical industry.

The first attachment part, such as the first spike, may be made of material comprising one or more of magnesium, titanium, iron and zinc. The material of the first attachment part/first spike may be biocompatible and/or biodegradable such as a biocompatible material and/or a biodegradable material. The material of the first attachment part/first spike may comprise one or more biodegradable polymers such as PLA and/or POLGA. Some of, part of, most of, substantially all, or all of the material of the first attachment part/first spike may be biocompatible and/or biodegradable. The material of the first attachment part, such as the first spike, may comprise, consist of, or essentially consist of, biocompatible and/or biodegradable material such as biocompatible and/or biodegradable metals. The material of the first attachment part, such as the first spike, may comprise a biodegradable or bioresorbable metal or metal alloy, such as magnesium, zinc, and/or iron or an alloy comprising one or more of magnesium, zinc and iron. A biodegradable or bioresorbable metal or metal alloy may be understood as a metal or metal alloy that degrades safely within e.g. a human body in a practical amount of time, for example related to their application. The material of the first attachment part, such as the first spike, may comprise one or more metals such as a combination of one or more metals e.g. as a metal alloy.

The second attachment part, such as the second spike, may be made of material comprising one or more of magnesium, titanium, iron and zinc. The material of the second attachment part/second spike may be biocompatible and/or biodegradable such as a biocompatible material and/or a biodegradable material. The material of the second attachment part/second spike may comprise one or more biodegradable polymers such as PLA and/or POLGA. Some of, part of, most of, substantially all, or all of the material of the second attachment part/second spike may be biocompatible and/or biodegradable. The material of the second attachment part, such as the second spike, may comprise, consist of, or essentially consist of, biocompatible and/or biodegradable material such as biocompatible and/or biodegradable metals. The material of the second attachment part, such as the second spike, may comprise a biodegradable or bioresorbable metal or metal alloy, such as magnesium, zinc, and/or iron or an alloy comprising one or more of magnesium, zinc and iron. A biodegradable or bioresorbable metal or metal alloy may be understood as a metal or metal alloy that degrades safely within e.g. a human body in a practical amount of time, for example related to their application. The material of the second attachment part, such as the second spike, may comprise one or more metals such as a combination of one or more metals e.g. as a metal alloy.

An advantage of having a biodegradable material used in the attachment part(s) may be that the delivery device is able to deliver an active drug substance or payload arranged in the attachment part(s) and/or body parts of the delivery device at a specific part of the body of the subject, e.g. such as the stomach or intestines after the delivery device has attached to the internal surface, e.g. the intestinal wall, thanks to the sharp properties of the material of the attachment part(s), and for an extended period of time, since the biodegradable material will degrade gradually in time. Further, when the material of the attachment part(s) is biodegradable, the attachment part(s) will degrade in the human body and disappear after having delivered the payload/active drug substance comprised in the drug delivery device, thereby avoiding harming the human subject over time. The attachment part(s) may be configured to degrade in a period of time of hours, e.g. 2 hours, 5 hours, 10 hours, 20 hours, or 24 hours, days, e.g. 1 day, 2 days, 5 days, or weeks, e.g. 1 week, 2 weeks, 3 weeks, or 5 weeks.

The material of the attachment part(s), such as the spike(s), may comprise one or more or a combination of magnesium (Mg), zinc (Zn), and/or iron (Fe). An advantage of having the attachment part(s) of a material comprising Mg, Zn, and/or Fe may be that the shape and size of the attachment part(s) can be precisely controlled thereby providing improved attachment to the internal surface, for example to an internal wall of the intestines of the human subject.

For example, the material of the attachment part(s), such as the spike(s), may comprise 0.001 wt. % to 100 wt % of biodegradable metal such as 0.001 wt % to 100 wt % of magnesium, 0.001 wt % to 100 wt % of zinc, 0.001 wt % to 100 wt % of iron.

The material of the attachment part(s), such as the spike(s), may for example comprise 0.001 wt. % of Mg, 0.005 wt. % of Mg, 0.01 wt. % of Mg, 0.05 wt. % of Mg, 0.1 wt. % of Mg, 0.5 wt. % of Mg, 1 wt. % of Mg, 5 wt. % of Mg, 10 wt. % of Mg, 20 wt. % of Mg, 30 wt. % of Mg, 40 wt. % of Mg, 50 wt. % of Mg, 60 wt. % of Mg, 70 wt. % of Mg, 80 wt. % of Mg, 90 wt. % of Mg, or 100 wt. % of Mg.

The material of the attachment part(s), such as the spike(s), may for example comprise 0.001 wt. % of Zn, 0.005 wt. % of Zn, 0.01 wt. % of Zn, 0.05 wt. % of Zn, 0.1 wt. % of Zn, 0.5 wt. % of Zn, 1 wt. % of Zn, 5 wt. % of Zn, 10 wt. % of Zn, 20 wt. % of Zn, 30 wt. % of Zn, 40 wt. % of Zn, 50 wt. % of Zn, 60 wt. % of Zn, 70 wt. % of Zn, 80 wt. % of Zn, 90 wt. % of Zn, or 100 wt. % of Zn.

The material of the attachment part(s), such as the spike(s), may for example comprise 0.001 wt. % of Fe, 0.005 wt. % of Fe, 0.01 wt. % of Fe, 0.05 wt. % of Fe, 0.1 wt. % of Fe, 0.5 wt. % of Fe, 1 wt. % of Fe, 5 wt. % of Fe, 10 wt. % of Fe, 20 wt. % of Fe, 30 wt. % of Fe, 40 wt. % of Fe, 50 wt. % of Fe, 60 wt. % of Fe, 70 wt. % of Fe, 80 wt. % of Fe, 90 wt. % of Fe, or 100 wt. % of Fe.

The material of the attachment part(s), such as the spike(s), may comprise a metal alloy such as Zn—Mg, Zn—Fe, Mg—Fe, or Zn—Mg—Fe. The material of the attachment part(s), such as the spike(s), may for example comprise an alloy of Zn—Mg with 0.001 wt. % of Mg, 0.005 wt. % of Mg, 0.01 wt. % of Mg, 0.05 wt. % of Mg, 0.1 wt. % of Mg, 0.5 wt. % of Mg, 1 wt. % of Mg, 5 wt. % of Mg, 10 wt. % of Mg, 20 wt. % of Mg, 30 wt. % of Mg, 40 wt. % of Mg, 50 wt. % of Mg, 60 wt. % of Mg, 70 wt. % of Mg, 80 wt. % of Mg, or 90 wt. % of Mg.

The material of the attachment part(s), such as the spike(s), may for example comprise an alloy of Zn—Fe with 0.001 wt. % of Fe, 0.005 wt. % of Fe, 0.01 wt. % of Fe, 0.05 wt. % of Fe, 0.1 wt. % of Fe, 0.5 wt. % of Fe, 1 wt. % of Fe, 5 wt. % of Fe, 10 wt. % of Fe, 20 wt. % of Fe, 30 wt. % of Fe, 40 wt. % of Fe, 50 wt. % of Fe, 60 wt. % of Fe, 70 wt. % of Fe, 80 wt. % of Fe, or 90 wt. % of Fe.

The material of the attachment part(s), such as the spike(s), may for example comprise an alloy of Mg—Fe with 0.001 wt. % of Fe, 0.005 wt. % of Fe, 0.01 wt. % of Fe, 0.05 wt. % of Fe, 0.1 wt. % of Fe, 0.5 wt. % of Fe, 1 wt. % of Fe, 5 wt. % of Fe, 10 wt. % of Fe, 20 wt. % of Fe, 30 wt. % of Fe, 40 wt. % of Fe, 50 wt. % of Fe, 60 wt. % of Fe, 70 wt. % of Fe, 80 wt. % of Fe, or 90 wt. % of Fe.

The material of the attachment part(s), such as the spike(s), may for example comprise an alloy of Zn—Mg—Fe with 0.001 wt. % of Fe, 0.005 wt. % of Fe, 0.01 wt. % of Fe, 0.05 wt. % of Fe, 0.1 wt. % of Fe, 0.5 wt. % of Fe, 1 wt. % of Fe, 5 wt. % of Fe, 10 wt. % of Fe, 20 wt. % of Fe, 30 wt. % of Fe, 40 wt. % of Fe, 50 wt. % of Fe, 60 wt. % of Fe, 70 wt. % of Fe, 80 wt. % of Fe, 90 wt. % of Fe, 0.001 wt. % of Mg, 0.005 wt. % of Mg, 0.01 wt. % of Mg, 0.05 wt. % of Mg, 0.1 wt. % of Mg, 0.5 wt. % of Mg, 1 wt. % of Mg, 5 wt. % of Mg, 10 wt. % of Mg, 20 wt. % of Mg, 30 wt. % of Mg, 40 wt. % of Mg, 50 wt. % of Mg, 60 wt. % of Mg, 70 wt. % of Mg, 80 wt. % of Mg, 90 wt. % of Mg, 0.001 wt. % of Zn, 0.005 wt. % of Zn, 0.01 wt. % of Zn, 0.05 wt. % of Zn, 0.1 wt. % of Zn, 0.5 wt. % of Zn, 1 wt. % of Zn, 5 wt. % of Zn, 10 wt. % of Zn, 20 wt. % of Zn, 30 wt. % of Zn, 40 wt. % of Zn, 50 wt. % of Zn, 60 wt. % of Zn, 70 wt. % of Zn, 80 wt. % of Zn, or 90 wt. % of Zn.

The attachment part(s), such as the spike(s), may be made of a material comprising one or more thermoplastic or thermoset polymers. The material of the attachment part(s), such as the spike(s), may comprise one or more active drug substances. Thus, an active drug substance may be embedded in the material of the attachment part(s), such as the spike(s), to form a pharmaceutical composition.

In some embodiments, the attachment part(s), such as the spike(s), may comprise for example water soluble, water insoluble, biodegradable, non-biodegradable and/or pH dependent soluble materials. In some embodiments, the attachment part(s), such as the spike(s), may comprise a water soluble, biodegradable and/or pH-dependent material that may dissolve and/or degrade so that the attachment part(s), such as the spike(s), lodged in the intestinal tissue may gradually degrade and/or dissolve. In some embodiments, the attachment part(s), such as the spike(s), may comprise a water-soluble material to allow immediate release or modified release of the active drug substance depending on the material selected. In some embodiments, a water insoluble or biodegradable material may allow depot of the active drug substance in the attachment part(s), such as the spike(s), for longer release duration (for example days, weeks or months). In some embodiments, a pH dependent soluble material may allow the attachment part(s), such as the spike(s), to stay intact at pH conditions below the physiologic for example a pH of approximately 7.4 to remain intact in the gastrointestinal lumen, but then may dissolve once inside the gastrointestinal wall. In some embodiments, one or more water soluble, water insoluble, biodegradable and/or pH dependent materials may optionally be combined to control release of the active drug substance for example by diffusion or erosion of the attachment part(s), such as the spike(s), for controlled release duration (for example minutes, hours, days, weeks, or months).

In some embodiments, the attachment part(s), such as the spike(s), may be made from different compositions. For example, an outer part of the attachment part(s), such as the spike(s), may be made of one composition and an inner core of the attachment part(s), such as the spike(s), may be made from another composition. In some embodiments, the outer part and the inner core of the attachment part(s), such as the spike(s), may be composed of for example a water soluble, a water insoluble, a biodegradable, and/or a pH dependent material. In some embodiments, one or more water soluble, water insoluble, biodegradable and/or pH dependent materials may be combined to control the release of the active drug substance once the attachment part(s), such as the spike(s), may move its position from the lumen to the internal tissue for example the gastrointestinal lumen to the gastrointestinal tissue.

In some embodiments, the attachment part(s), such as the spike(s), may be tubular and may include a tubular body and the tubular body may comprise an active drug substance for example a liquid payload comprising the active drug substance, optionally connected to a tubular attachment part so the payload with the active drug substance may flow though the attachment part(s), such as the spike(s), into the internal tissue for example the intestinal tissue. In some embodiments, the tubular body may contain expandable such as swelling excipients that may expand by a chemical reaction for example when mixed expand in volume and/or produce a gas to advance the delivery of the payload. In some embodiments, the expansion is by osmosis.

In some embodiments, the first compartment (compartment to hold active drug substance) may comprise a closure part for closing the first compartment. The closure part may contribute to improved control of release of the active drug substance. In some embodiments, the closure part may be composed of for example a water soluble, a water insoluble, a biodegradable, and/or a pH dependent material. In some embodiments, one or more water soluble, water insoluble, biodegradable and/or pH dependent materials may be combined to control the release of the active drug substance from the first compartment once the attachment part(s), such as the spike(s), moves its position from the lumen to the internal tissue for example from the gastrointestinal lumen to the gastrointestinal tissue.

FIG. 1 shows a view of a drug delivery device in accordance with the disclosure. As shown, the drug delivery device 100 can include an insert 200 (covered by cover element 300) inserted into a carrier 101. The drug delivery device 100 can include a central axis 103. The carrier can include a first body part 104 and a second body part 102. The first body part 104 and the second body part 102 can rotate with respect to one another around the central axis 103.

Figure 2:
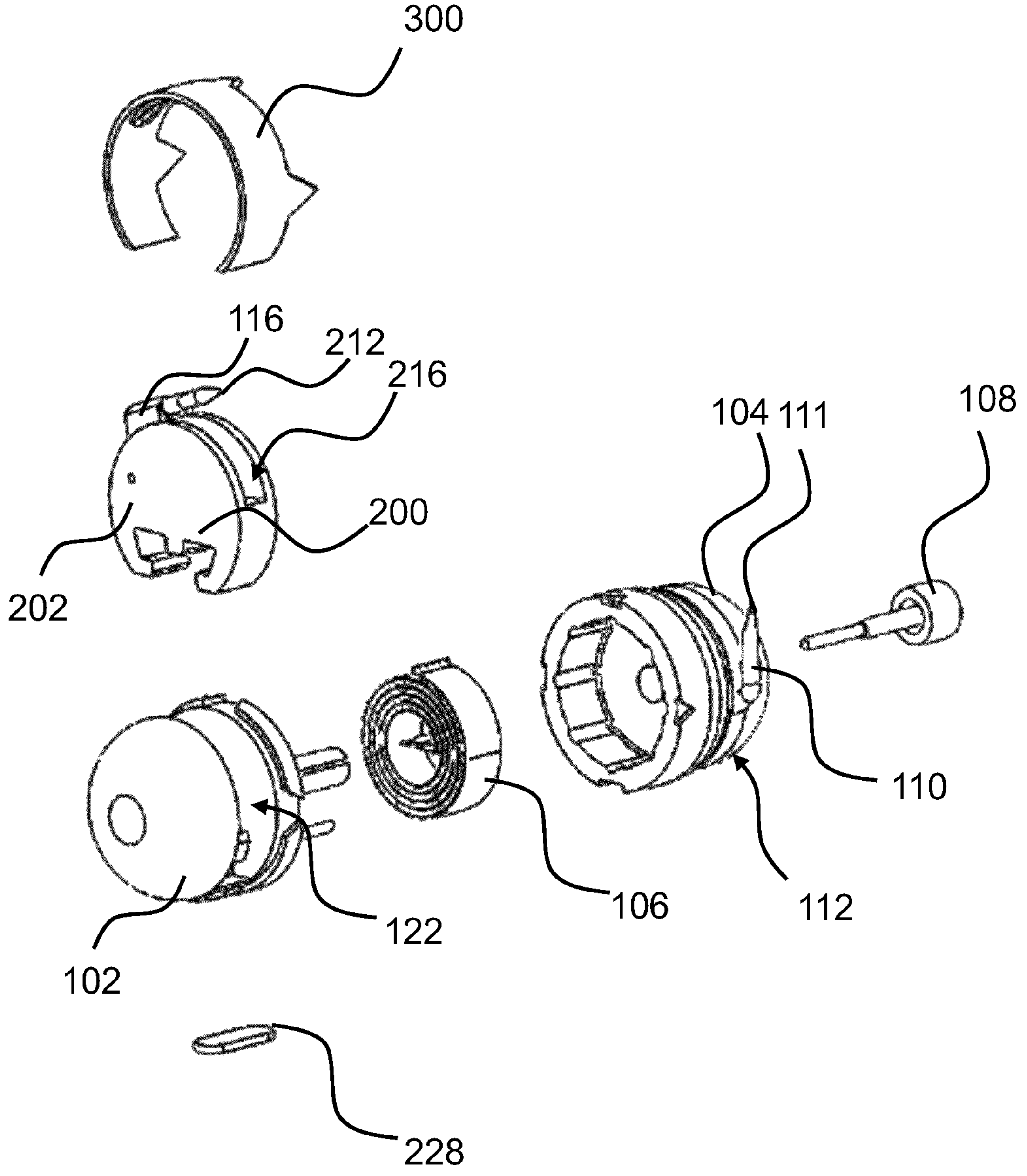
FIG. 2 shows an exploded view of an exemplary drug delivery device.

FIG. 2 shows an exploded view of the drug delivery device 100. As shown, the first body part 104 can include a first recess 112. The carrier can further include a first attachment part 110 attached to the first body part 104 and having a first distal end 111. The first attachment part 110 can be contained within the first recess 112 and can extend out of the first recess 112 after rotation of the first body part 104.

The second body part 102 can include a second recess 122. The second recess 122 can be configured to releasably receive the insert 200. The insert 200 can be configured to be inserted and fixed in the second recess 122. For example, the insert 200 can be inserted into the second recess 122 via an opening of the outer surface of the second body 102. Thus, the insert 200 can form a closed outer surface of the second body 102. The second recess 122 can extend perpendicular to the central axis 103.

The insert can include a second attachment part 116 and an insert body 202 with an insert recess 216. The second attachment part 116 can include a second distal end 212. Similar to the first attachment part 110, the second attachment part 116 can be retained within the insert recess 216 and can extend out of the insert recess 216 when the second body part 102 is rotated. Thus, when the first body part 104 and second body part 102 rotate, the first attachment part 110 and the second attachment part 116 extend outwards with distal ends 212/111 facing one another to attach the drug delivery device 100 into tissue. The first attachment part 110 and the second attachment part 116 can include a first spike and a second spike, respectively.

When inserted into the carrier 101, the insert 200 can form an outer surface of the drug delivery device 100. Thus, the insert 200 can be inserted into the second recess 122 of the carrier 101 to form the drug delivery device 100 as shown in FIG. 1. The insert 200 can also be removed from the carrier 101 and refilled or replaced with a different insert 200. Thus the carrier 101 can be reused multiple times as needed.

As shown in FIG. 2, the first body part 104 and the second body part 102 can be connected via an axle 108. Further, the carrier can contain an actuator mechanism 106 configured to rotate at least one of the first body part 104 or the second body part 102 with respect to one another about the central axis 103. Specifically, the actuator mechanism 106 reduces the distance between the first distal end 111 and the second distal end 212 during rotation of the first body part 104 with respect to the second body part 102 around the central axis 103. Further, the actuator mechanism 306 is configured to move the first distal end 111 toward the second distal end 212. The actuator mechanism 306 can be a resilient part.

Thus, the drug delivery device 100 has a first state where the first attachment part 110 and the second attachment part 116 are rotationally stationary relative to each other and a second state where the first attachment part 110 and the second attachment part 116 are rotationally mobile relative to each other.

The drug delivery device 100 can also include a locking mechanism 228 configured to lock the first body part 104 in relation to the insert 200 in a first state of the drug delivery device 100. The locking mechanism 228 can fit as a connection between the first body part 104 and the second body part 102, preventing motion. When the locking mechanism 228 dissolves after a particular time period, the first and second body parts 104/102 can rotate with respect to one another.

Further, the carrier 101 for the drug delivery device 100 comprising the insert 200 and the carrier 101 can include the first body part 104 having the first recess 112, a first attachment part 110 attached to the first body part 104 and having a first distal end 111, and a second body part 102 having a second recess 122, the second recess 122 defining an opening on an outer surface of the second body part 102. The carrier 101 can further include an actuator mechanism 106 configured to rotate at least one of the first body part 104 or the second body part 102 with respect to one another about the central axis 103. The second recess 122 can be configured to fixedly receive the insert 200 having the second attachment part 116.

Figure 3:
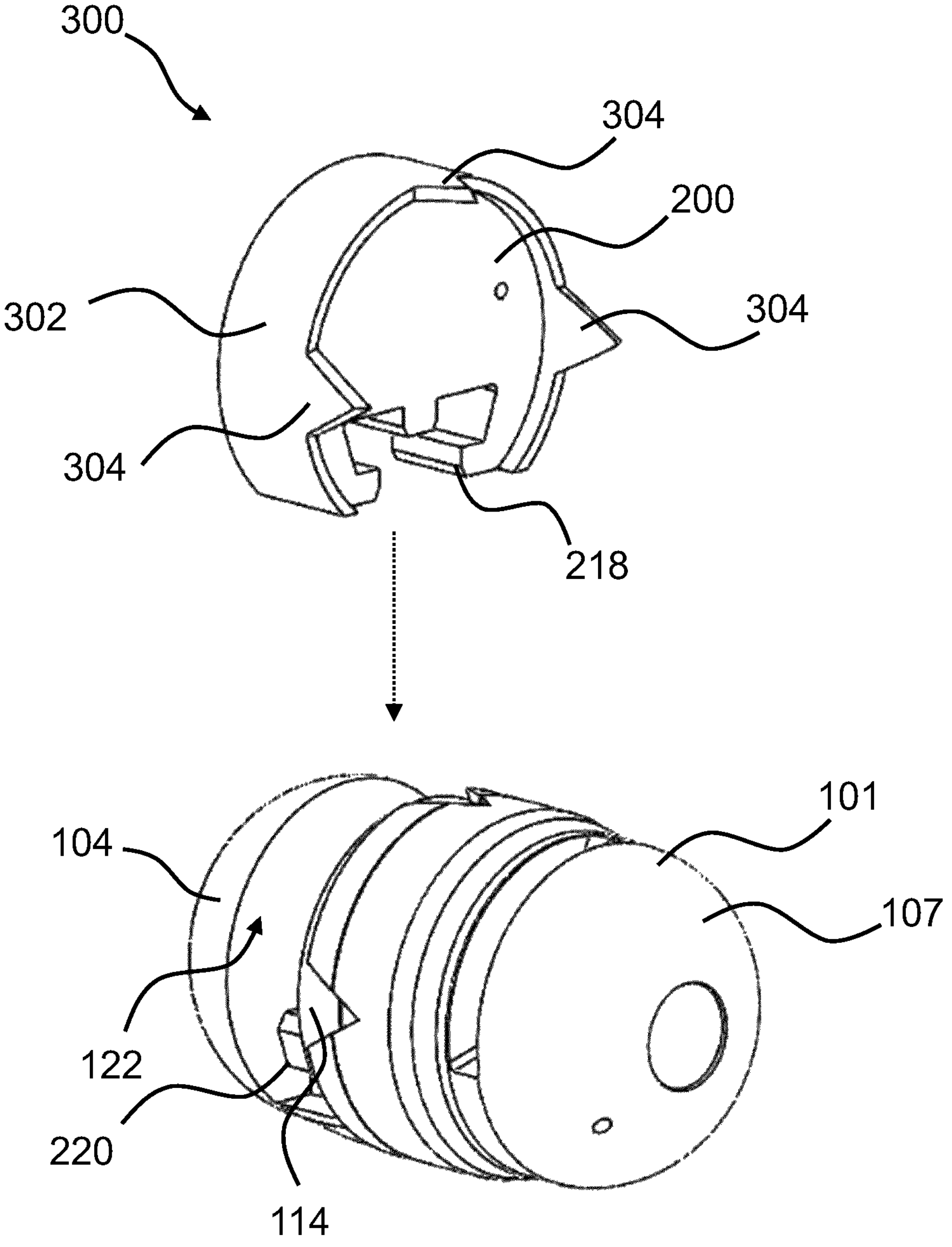
FIG. 3 shows a perspective view of an exemplary drug delivery device and an insert.

While FIG. 2 shows the cover element 300 removed from the insert 200, FIG. 3 shows the cover element 300 attached so that the insert 200 and cover element 300 are ready to be inserted into the carrier 101, in particular into second recess 122. As shown, the cover element 300 can fit around an outer surface of the insert 200, for example by snap fitting over an outer surface of the insert 200.

The insert 200 can include an insert mating element 218 configured to mate with a mating feature 220 within second recess 122 of the carrier 101. The mating element 218 can be located on a bottom surface of the insert 200. The mating feature 220 may be located on a bottom surface of the second recess 122. As shown, the inert body 202 can be snap fit to the second body part 102 within the second recess 122. The insert 200 can be removed from the carrier 101 by applying enough force to separate the mating element 218 from the mating feature 220. Thus, the insert 200 is releasably retained within the carrier 101.

As shown in FIG. 3, the cover element 300 can include a cover element body 302. The cover element 300 can at least partially cover the second attachment part 116 and be configured to prevent motion of the second attachment part 116. One or more locking protrusions 304 can extend from the cover element body 302. In the cover element shown in FIG. 3, the cover element 300 can contain three triangular locking protrusions 304. The locking protrusions 304 all extend the same away from the cover element body 302.

The at least one protrusion 304 is configured to mate with a slot 114 (e.g., mating feature) on the first body part 104 and/or the second body part 102. This can lock the first body part 104 with respect to the second body part 102. Thus, rotational motion between the first body part 104 and/or the second body part 102 can be prevented until release of the cover element 300. Accordingly, the cover element 300 can act as a second lock with locking mechanism 228. Alternatively, the locking mechanism 228 may not be used. The cover element 300 may also be dissolvable, and once dissolved the actuator mechanism 106 can rotate the second body part 102 with respect to the first body part 104, thus attaching the drug delivery system to tissue.

Figure 4:
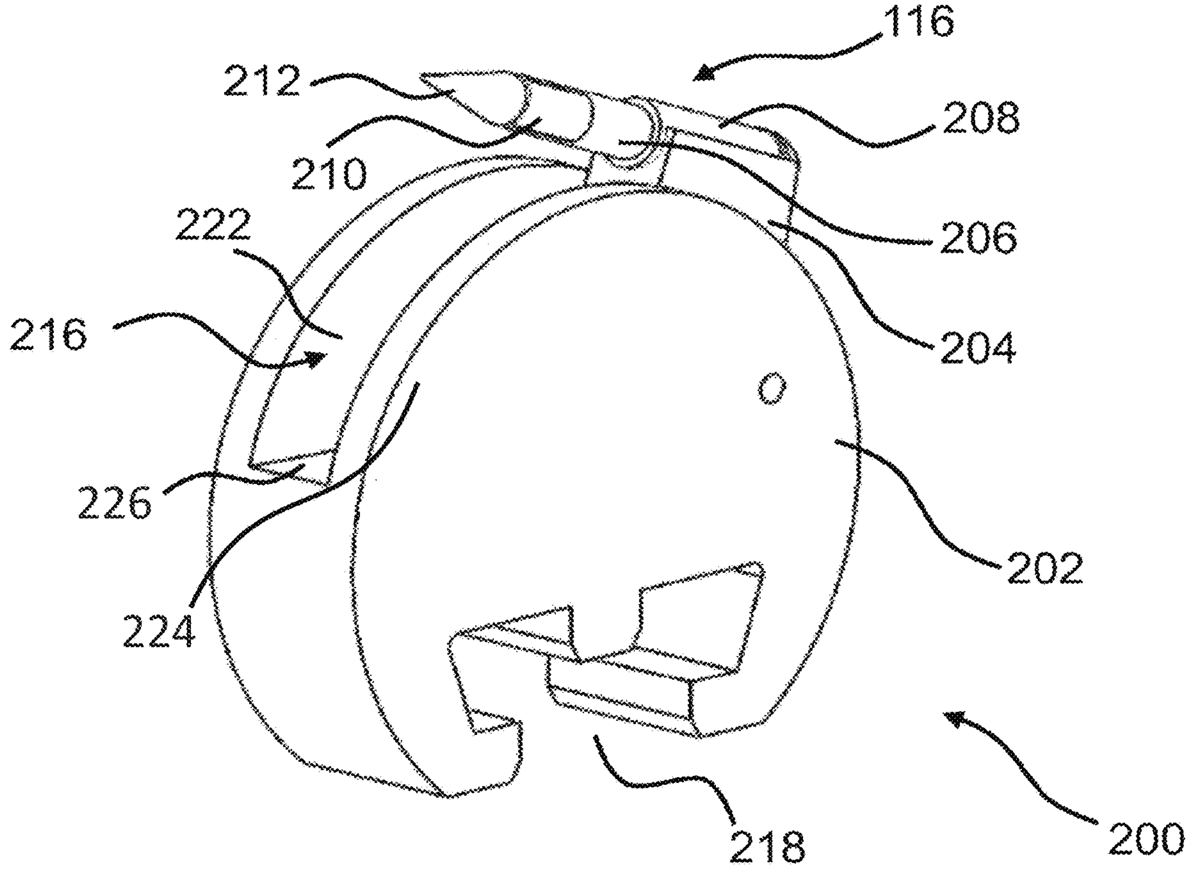
FIG. 4 shows a view of an exemplary drug delivery device.
Figure 5:
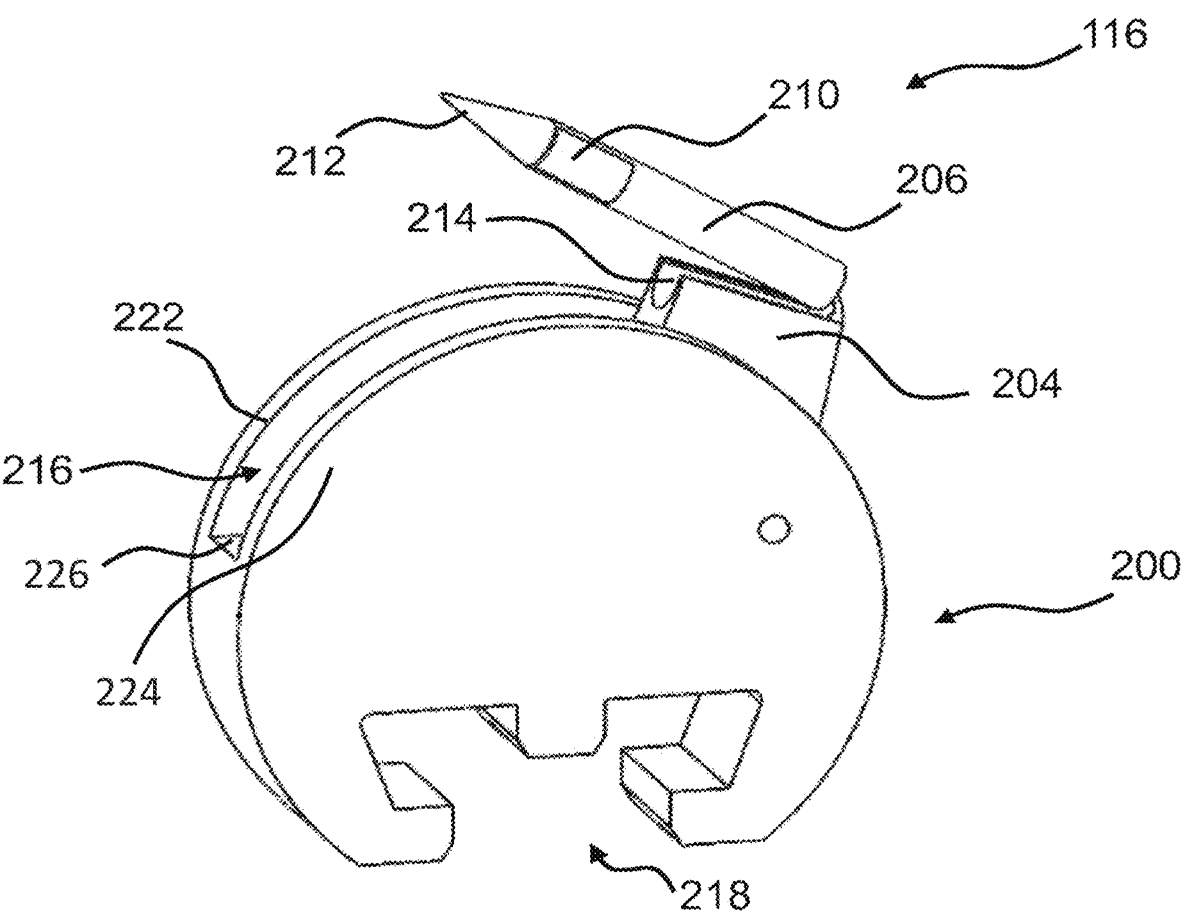
FIG. 5 shows a view of an exemplary insert.
Figure 6:
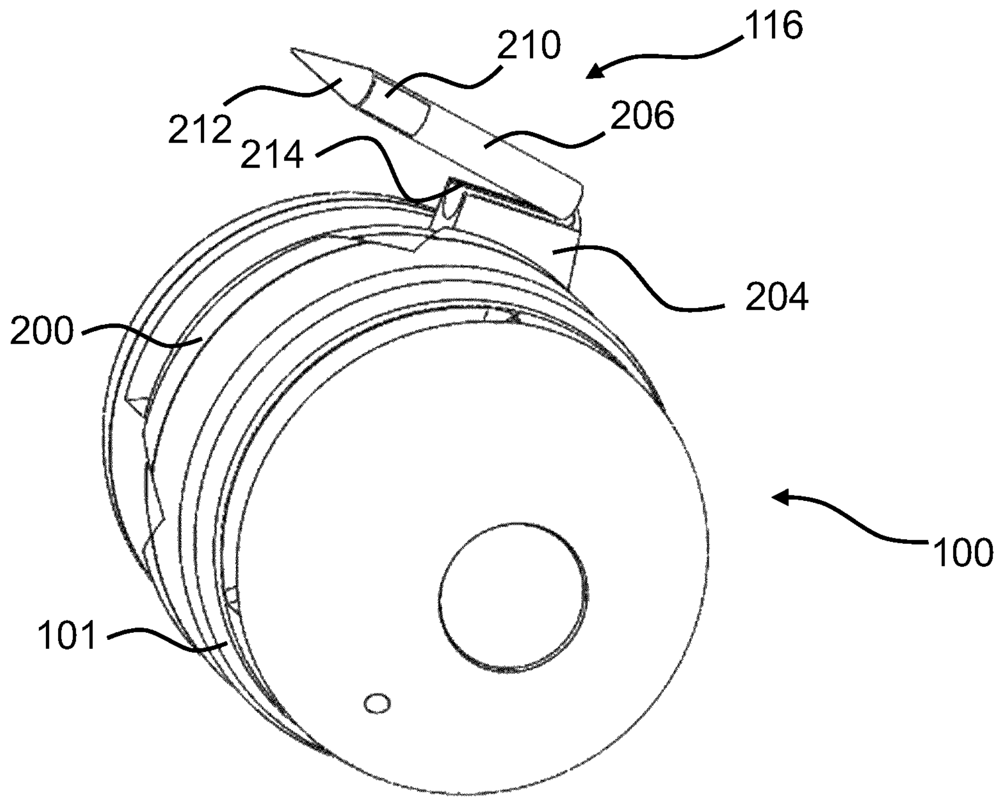
FIG. 6 shows a view of an exemplary insert.

FIG. 4, FIG. 5, and FIG. 6 illustrate a drug delivery device 100 and insert 200 where a component of the second attachment part 116 can be released. This can advantageously allow the drug delivery device 100 to be removed from a patient while an active drug substance can continue being applied to a patient.

Specifically, FIG. 4 illustrates the insert 200 with the second attachment part 116 still attached. As shown, the second attachment part 116 can include a spike 206 with a second distal end 212 and an arm 204. The arm 204 can have an arm distal end with a spike holder 208 (shown in FIG. 5) located on the arm distal end. The spike 206 can be attached to the spike holder 208. The spike 206 and/or the spike holder 208 may be held with a cradle 214 of the arm 204. The spike 206 may contain a chamber 210 for holding an active drug substance. Thus, the second attachment part 116 may include the chamber 210.

Advantageously, the arm 204 can be rotatable within the insert recess 216 about a second rotation axis. Thus, the spike 206 can be located within the insert recess 216 (such as covered by cover element 300) and then can be rotated out of the insert recess 216 to attach to tissue. The insert recess 216 can be formed by two opposing sidewalls of the insert body 202. Specifically, the insert recess 216 can be formed by a first side wall 222, a second side wall 224, and a bottom 226.

The spike holder 208 may be made of a dissolvable material. Thus, after a time period the spike holder 208 may dissolve to release the spike 206 from the arm 204. This releasing is shown in the insert 200 of FIG. 5, and with respect to the whole drug delivery device 100 in FIG. 6. Accordingly, the spike 206 can remain in a patient tissue to continue to apply the active drug substance while the remainder of the drug delivery device 100 can continue to pass through the patient to be retrieved and reused. The spike 206 can then be replaced, or the whole insert 200 can be replaced into the carrier 101. This can greatly increase the speed a particular drug delivery device can be used.

Thus, as shown in FIG. 4, the insert 200 for the drug delivery device 100 made up of the carrier 101 and the insert 200 can include an insert body 202 configured to be fixably arranged within a recess (such as second recess 122) of the drug delivery device 100. The inert 200 can further include an attachment part (such as second attachment part 116) rotatably attached to the insert body 202 and having a distal end (such as second distal end 212). The insert 200 can further include a cover element 300 attached to the insert body 202 and configured to at least partially cover and prevent rotation of the attachment part (such as second attachment part 116).

Figure 7:
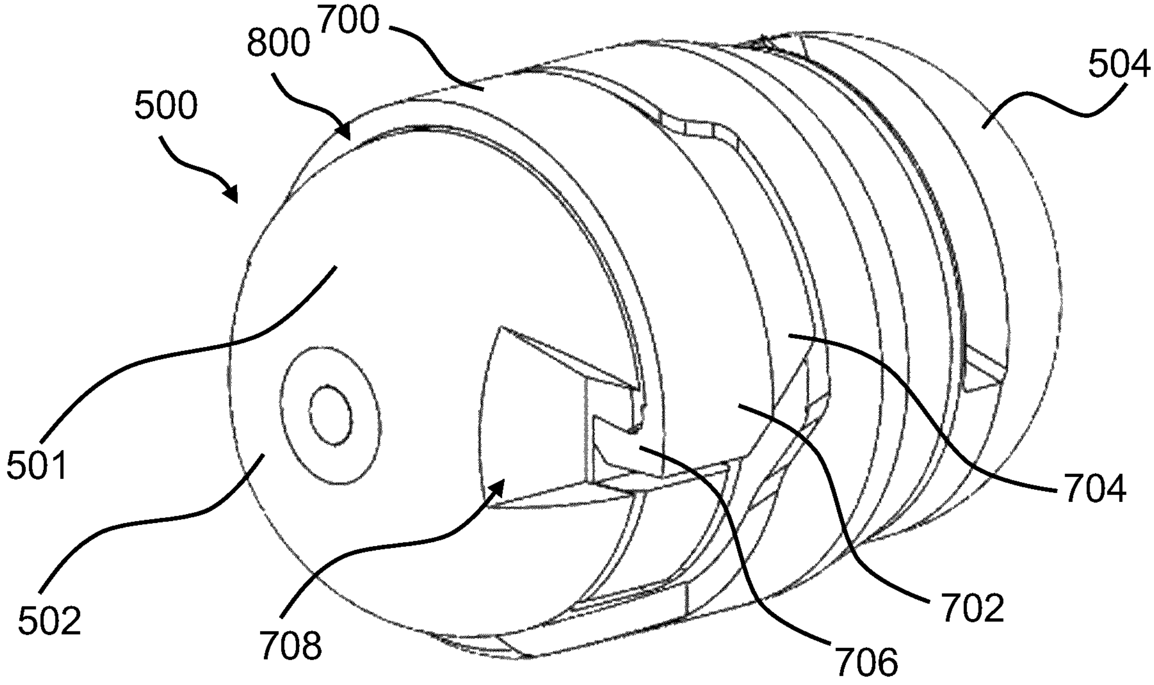
FIG. 7 shows a view of an alternate exemplary drug delivery device.

FIG. 7 illustrates an alternate drug delivery device. The drug delivery device/carrier/insert 500/501/800 can include any and/or all of the features discussed above with relation to drug delivery device/carrier/insert 100/101/200 unless otherwise specified. As shown, the drug delivery device 500 can be a carrier 501 with an insert 800 inserted. The carrier 501 can include a first body part 504 and a second body part 502. The insert 800 can be covered by cover element 700. The carrier 501 can include a longitudinal slot 708, which can allow the cover element 700 to slide longitudinally and uncover the second attachment element.

Figure 8:
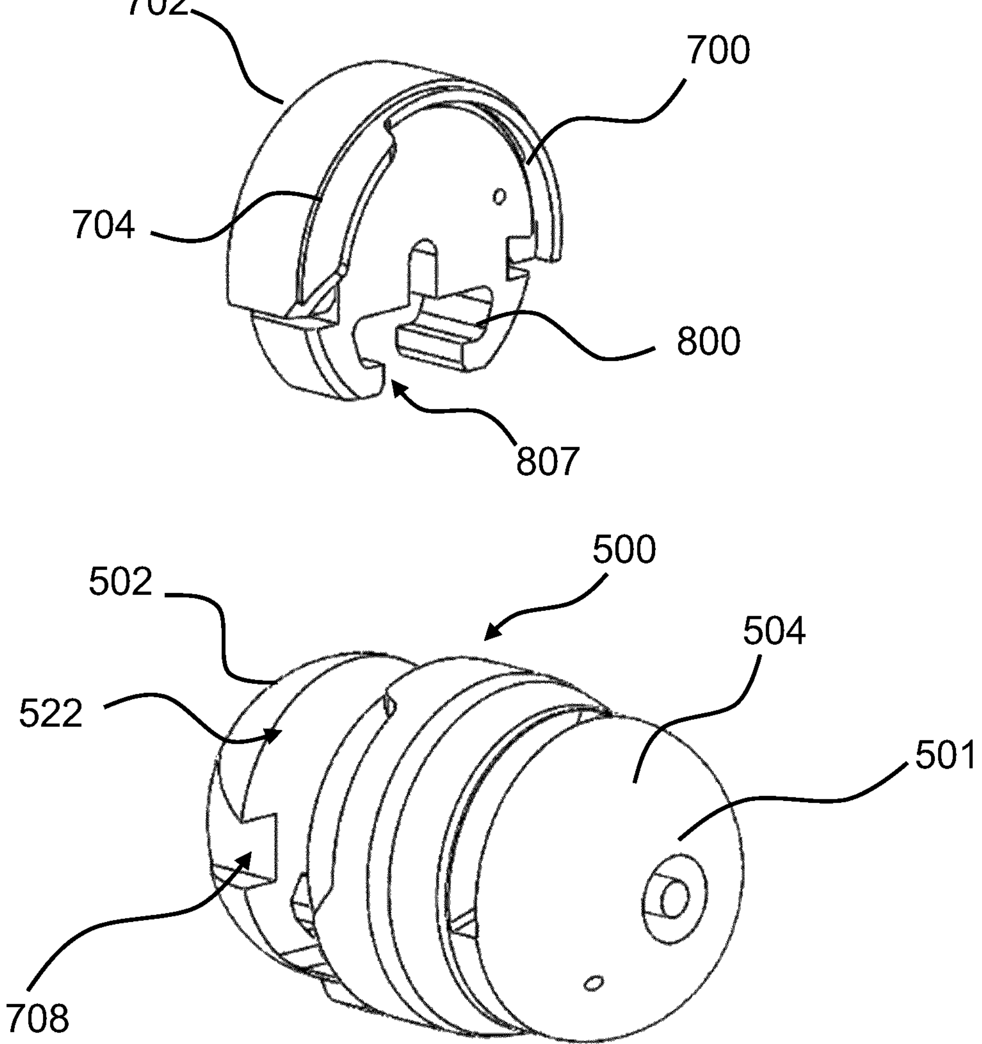
FIGS. 8-10 show a perspective view of an alternate exemplary drug delivery device and an alternate insert.

FIG. 8 illustrates view of drug delivery device 500 with the insert 600 removed from the second recess 522 of carrier 501. As shown, the cover element 700 can include a cover element body 702 and a locking protrusion 704. The locking protrusion can mate with mating feature 508 of the carrier 501. Unlike the previous cover element 300, cover element 700 includes a single locking protrusion 704. The single locking protrusion 704 is trapezoidal in shape and extends over a larger circumference of the cover element 700.

Figures 9, 10:
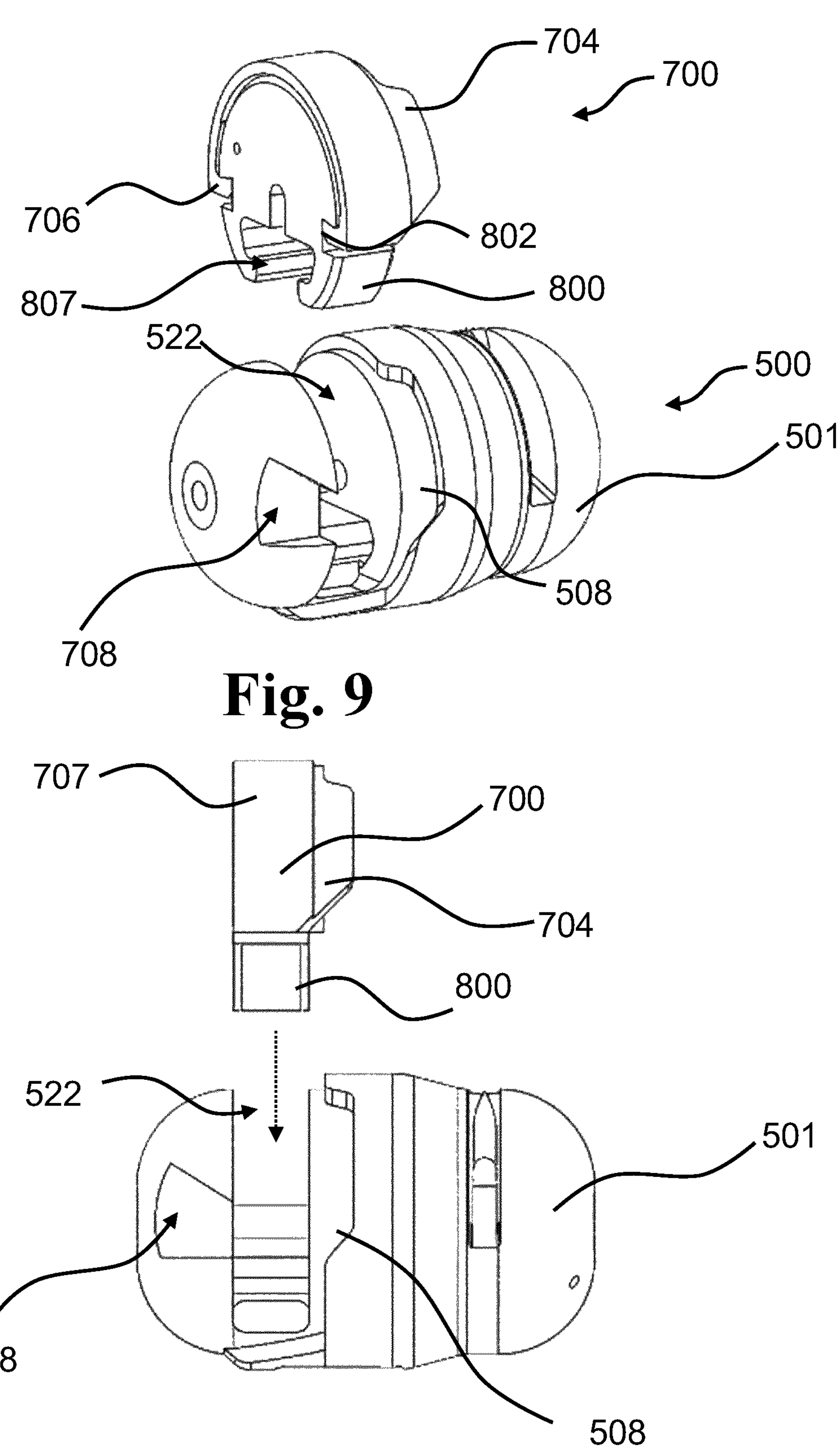

Further, as shown in FIG. 9, unlike the cover element 300, the cover element 700 can include a cover attachment element 706 which can mate with insert mating element 802 of the insert 800. As shown, the insert mating element 802 can be a slot to receive a portion of the cover attachment element 706, thus retaining the cover element 700 to the insert 800. FIG. 10 illustrates a side view of the carrier 501 with the insert 800 removed.

Figure 11:
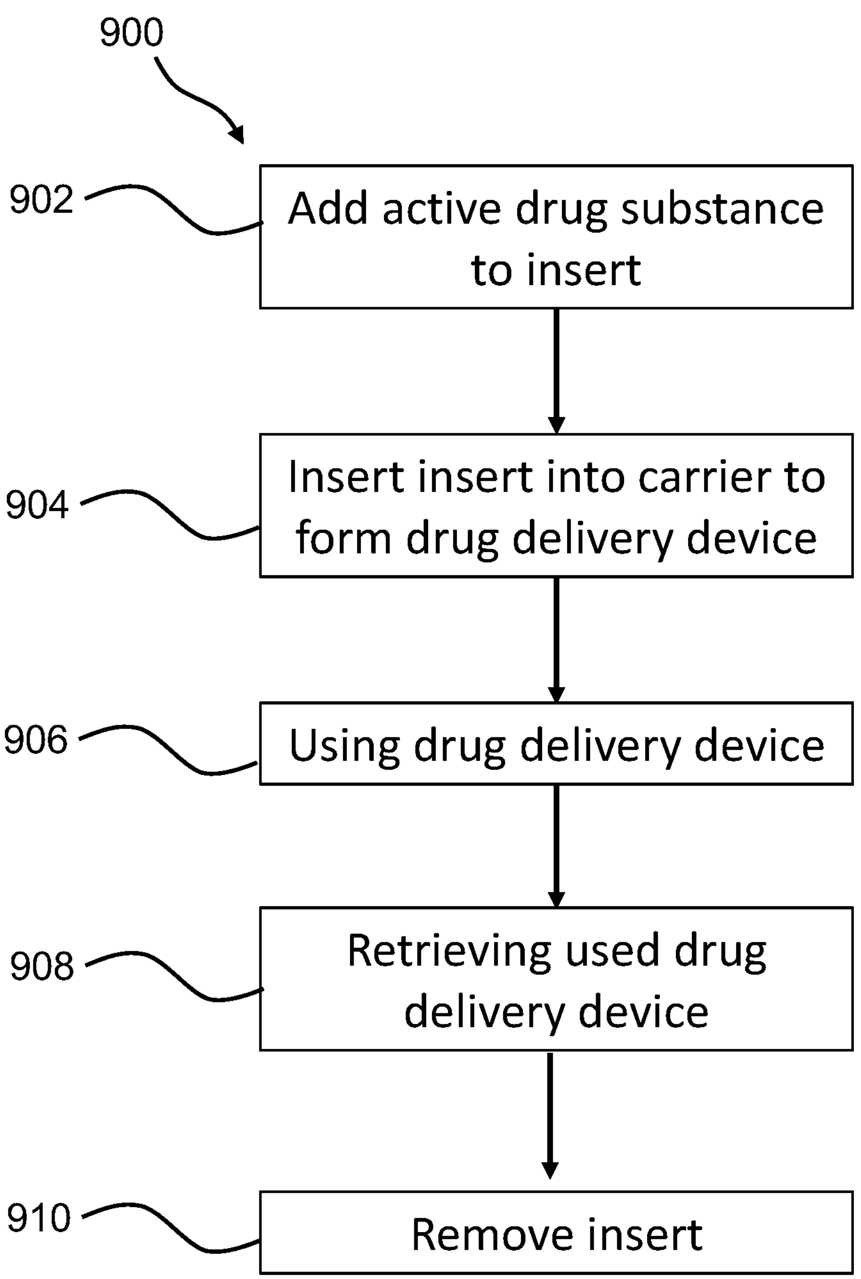
FIG. 11 shows an embodiment of a method of use of the drug delivery device.

FIG. 11 illustrates a method of using any one of the drug delivery devices disclosed herein. The method 900 includes adding an active drug substance to an insert 902. Following, the insert can be inserted into a carrier to form a drug delivery device 904. The drug delivery device can then be used 906, such as by a patient ingesting the drug delivery device. Once the drug delivery device has passed through the patient, it may be retrieved 908 and the insert may be removed from the carrier 910. A new insert can optionally be inserted into the carrier.

Also disclosed are delivery devices, methods, and compositions according to any of the following items.

Item 1. A drug delivery device having an axis, the drug delivery device comprising a carrier and an insert, the carrier comprising:

a first body part having a first recess;

a first attachment part attached to the first body part and having a first distal end;

a second body part having a second recess;

an actuator mechanism configured to rotate at least one of the first body part or the second body part with respect to one another about the axis; and an insert configured to be inserted and fixed in the second recess, the insert comprising a second attachment part and an insert body with an insert recess, the second attachment part having a second distal end.

Item 2. Drug delivery device according to Item 1, wherein the insert forms an outer surface of the drug delivery device.

Item 3. Drug delivery device according to any of Items 1-2, wherein the actuator mechanism reduces the distance between the first distal end and the second distal end during rotation of the first body part with respect to the second body part around the axis.

Item 4. Drug delivery device according to any of Items 1-3, wherein the second recess extends perpendicular to the axis.

Item 5. Drug delivery device according to any of Items 1-4, wherein the second attachment part comprises a spike and an arm, the arm having an arm distal end with a spike holder located on the arm distal end, wherein the spike is attached to the spike holder.

Item 6. Drug delivery device according to Item 5, wherein the arm is rotatable within an insert recess about a second rotation axis, and wherein the insert recess is formed by two opposing sidewalls of the insert body.

Item 7. Drug delivery device according to any of Items 1-6, wherein the insert is configured to be inserted into the second recess via an opening of the outer surface of the second body.

Item 8. Drug delivery device according to any of Items 1-7, wherein the insert body is configured to be snap fit to the second body part within the second recess.

Item 9. Drug delivery device according to any of Items 1-8, wherein the second attachment part comprises a chamber for holding an active drug substance.

Item 10. Drug delivery device according to any of Items 1-9, the insert comprising a cover element at least partially covering the second attachment part and configured to prevent motion of the second attachment part.

Item 11. Drug delivery device according to Item 10, wherein the cover element comprises at least one protrusion configured to mate with a slot on the first body part and/or the second body part.

Item 12. Drug delivery device according to any of Items 1-11, wherein the actuator mechanism comprises a resilient part.

Item 13. Drug delivery device according to any of Items 1-12, wherein the first attachment part and the second attachment part comprises a first spike and a second spike, respectively.

Item 14. Drug delivery device according to any of Items 1-13, further comprising a third attachment part attached to the first body part or the second body part and having a third distal end.

Item 15. Drug delivery device according to any of Items 1-14, wherein the actuator mechanism is configured to move the first distal end towards the second distal end.

Item 16. Drug delivery device according to any of Items 1-15, wherein the drug delivery device has a first state where the first attachment part and the second attachment part are rotationally stationary relative to each other and a second state where the first attachment part and the second attachment part are rotationally mobile relative to each other.

Item 17. Drug delivery device according to any of Items 1-16, wherein the drug delivery device comprises a locking mechanism configured to lock the first body part in relation to the insert in a first state of the drug delivery device.

Item 18. A carrier for a drug delivery device comprising an insert and the carrier, the carrier comprising:

a first body part having a first recess;

a first attachment part attached to the first body part and having a first distal end;

a second body part having a second recess, the second recess defining an opening on an outer surface of the second body part; and an actuator mechanism configured to rotate at least one of the first body part or the second body part with respect to one another about an axis, wherein the second recess is configured to fixedly receive the insert comprising a second attachment part.

Item 19. An insert for a drug delivery device comprising a carrier and the insert, the insert comprising:

an insert body configured to be fixably arranged within a recess of the drug delivery device;

an attachment part rotatably attached to the insert body and having a distal end;

a chamber configured to accommodate an active drug substance, wherein the chamber is in fluid communication with the attachment part; and a cover element attached to the insert body and configured to at least partially cover and prevent rotation of the attachment part.

The use of the terms “first”, “second”, “third” and “fourth”, “primary”, “secondary”, “tertiary” etc. does not imply any particular order, but are included to identify individual elements. Moreover, the use of the terms “first”, “second”, “third” and “fourth”, “primary”, “secondary”, “tertiary” etc. does not denote any order or importance, but rather the terms “first”, “second”, “third” and “fourth”, “primary”, “secondary”, “tertiary” etc. are used to distinguish one element from another. Note that the words “first”, “second”, “third” and “fourth”, “primary”, “secondary”, “tertiary” etc. are used here and elsewhere for labelling purposes only and are not intended to denote any specific spatial or temporal ordering.

Furthermore, the labelling of a first element does not imply the presence of a second element and vice versa.

It is to be noted that the word “comprising” does not necessarily exclude the presence of other elements or steps than those listed.

It is to be noted that the words “a” or “an” preceding an element do not exclude the presence of a plurality of such elements.

It should further be noted that any reference signs do not limit the scope of the claims, that the exemplary embodiments may be implemented at least in part by means of both hardware and software, and that several “means”, “units” or “devices” may be represented by the same item of hardware.

Language of degree used herein, such as the terms “approximately,” “about,” “generally,” and “substantially” as used herein represent a value, amount, or characteristic close to the stated value, amount, or characteristic that still performs a desired function or achieves a desired result. For example, the terms “approximately”, “about”, “generally,” and “substantially” may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES

100 drug delivery device
101 carrier
102 second body part
103 central axis
104 first body part
106 actuator mechanism
108 axle
110 first attachment part
111 first distal end
112 first recess
114 slot
116 second attachment part
122 second recess
200 insert
202 insert body
204 arm
206 spike
208 spike holder
210 chamber
212 second distal end
214 cradle
216 insert recess
218 insert mating element
222 first side wall
224 second side wall
226 bottom
228 locking mechanism
300 cover element
302 cover element body
304 locking protrusion
500 drug delivery device
501 carrier
502 second body part
504 first body part
508 mating feature
522 second recess
700 cover element
702 cover element body
704 locking protrusion
706 cover attachment element
708 longitudinal slot
800 insert
802 insert mating element
900 method
902 adding active drug substance to insert
904 inserting insert into carrier to form drug delivery device
906 using drug delivery device
908 retrieving used drug delivery device
910 removing insert

The invention claimed is:

1. A drug delivery device having an axis, the drug delivery device comprising a carrier and an insert, wherein the carrier comprises:

a first body part having a first recess;

a first attachment part attached to the first body part and having a first distal end;

a second body part having a second recess;

an actuator mechanism configured to rotate at least one of the first body part or the second body part with respect to one another about the axis; and the insert configured to be inserted and fixed in the second recess, wherein the insert comprises a second attachment part and an insert body with an insert recess, the second attachment part having a second distal end.

2. The drug delivery device according to claim 1, wherein the insert forms an outer surface of the drug delivery device.

3. The drug delivery device according to claim 1, wherein the actuator mechanism reduces a distance between the first distal end and the second distal end during rotation of the first body part with respect to the second body part around the axis.

4. The drug delivery device according to claim 1, wherein the second recess extends perpendicular to the axis.

5. The drug delivery device according to claim 1, wherein the second attachment part comprises a spike and an arm, the arm having an arm distal end with a spike holder located on the arm distal end, and wherein the spike is attached to the spike holder.

6. The drug delivery device according to claim 5, wherein the arm is rotatable within the insert recess about a second rotation axis, and wherein the insert recess is formed by two opposing sidewalls of the insert body.

7. The drug delivery device according to claim 1, wherein the insert is configured to be inserted into the second recess via an opening of an outer surface of the second body part.

8. The drug delivery device according to claim 1, wherein the insert body is configured to be snap fit to the second body part within the second recess.

9. The drug delivery device according to claim 1, wherein the second attachment part comprises a chamber for holding an active drug substance.

10. The drug delivery device according to claim 1, wherein the insert comprises a cover element at least partially covering the second attachment part, which is configured to prevent motion of the second attachment part.

11. The drug delivery device according to claim 10, wherein the cover element comprises at least one protrusion configured to mate with a slot on the first body part and/or the second body part.

12. The drug delivery device according to claim 1, wherein the actuator mechanism comprises a resilient part.

13. The drug delivery device according to claim 1, wherein the first attachment part and the second attachment part comprise a first spike and a second spike, respectively.

14. The drug delivery device according to claim 1, wherein the actuator mechanism is configured to move the first distal end towards the second distal end.

15. The drug delivery device according to claim 1, wherein the drug delivery device has a first state where the first attachment part and the second attachment part are rotationally stationary relative to each other and a second state where the first attachment part and the second attachment part are rotationally mobile relative to each other.

16. The drug delivery device according to claim 1, wherein the drug delivery device comprises a cover configured to lock the first body part in relation to the insert in a first state of the drug delivery device.

* * * * *